United States Patent
Schmitt et al.

(10) Patent No.: US 8,457,722 B2
(45) Date of Patent: Jun. 4, 2013

(54) DEVICE AND METHOD FOR MONITORING BODY FLUID AND ELECTROLYTE DISORDERS

(75) Inventors: Joseph M. Schmitt, Andover, MA (US); Martin Debreczeny, Danville, CA (US)

(73) Assignee: Covidien LP, Mansfield, MA (US)

( * ) Notice: Subject to any disclaimer, the term of this patent is extended or adjusted under 35 U.S.C. 154(b) by 1079 days.

(21) Appl. No.: 11/239,815

(22) Filed: Sep. 30, 2005

(65) Prior Publication Data

US 2006/0084864 A1    Apr. 20, 2006

Related U.S. Application Data

(63) Continuation of application No. 10/699,610, filed on Oct. 30, 2003, now Pat. No. 7,239,902, which is a continuation-in-part of application No. 10/441,943, filed on May 20, 2003, now Pat. No. 7,236,811, which is a continuation of application No. 09/810,918, filed on Mar. 16, 2001, now Pat. No. 6,591,122.

(51) Int. Cl.
*A61B 6/00* (2006.01)

(52) U.S. Cl.
USPC ........... 600/473; 600/310; 600/322; 600/475; 600/476; 600/477

(58) Field of Classification Search
USPC ................. 600/310, 316, 322, 473, 475, 547; 250/339.1, 341.8
See application file for complete search history.

(56) References Cited

U.S. PATENT DOCUMENTS

| | | | |
|---|---|---|---|
| 3,998,550 A | 12/1976 | Konishi et al. | |
| 4,066,068 A | 1/1978 | Nilsson et al. | |

(Continued)

FOREIGN PATENT DOCUMENTS

| | | |
|---|---|---|
| CA | 2353007 A1 | 6/2000 |
| DE | 19855521 A1 | 6/2000 |

(Continued)

OTHER PUBLICATIONS

Wheeler, Owen H., "Near Infrared Spectra of Organic Compounds," Department of Chemistry, College of Agriculture and Mechanic Arts, University of Puerto Rico (Mar. 1929).

(Continued)

*Primary Examiner* — Long V. Le
*Assistant Examiner* — Bradley Impink
(74) *Attorney, Agent, or Firm* — Fletcher Yoder

(57) ABSTRACT

Devices and methods for measuring body fluid-related metric using spectrophotometry that may be used to facilitate diagnosis and therapeutic interventions aimed at restoring body fluid balance. In one embodiment, the present invention provides a device for measuring a body-tissue water content metric as a fraction of the fat-free tissue content of a patient using optical spectrophotometry. The device includes a probe housing configured to be placed near a tissue location which is being monitored; light emission optics connected to the housing and configured to direct radiation at the tissue location; light detection optics connected to the housing and configured to receive radiation from the tissue location; and a processing device configured to process radiation from the light emission optics and the light detection optics to compute the metric where the metric includes a ratio of the water content of a portion of patient's tissue in relation to the lean or fat-free content of a portion of patient's tissue.

16 Claims, 7 Drawing Sheets

U.S. PATENT DOCUMENTS

| | | | |
|---|---|---|---|
| 4,364,008 A | 12/1982 | Jacques | |
| 4,711,244 A | 12/1987 | Kuzara | |
| 4,723,554 A | 2/1988 | Oman et al. | |
| 4,805,365 A | 2/1989 | Bastian | |
| 4,850,365 A | 7/1989 | Rosenthal | |
| 4,860,753 A | 8/1989 | Amerena | |
| 4,883,055 A | 11/1989 | Merrick | |
| 4,907,594 A | 3/1990 | Muz | |
| 5,057,695 A | 10/1991 | Hirao et al. | |
| 5,077,476 A | 12/1991 | Rosenthal | |
| 5,086,781 A | 2/1992 | Bookspan | |
| 5,111,817 A | 5/1992 | Clark et al. | |
| 5,146,091 A | 9/1992 | Knudson | |
| 5,224,478 A | 7/1993 | Sakai et al. | |
| 5,277,181 A | 1/1994 | Mendelson et al. | |
| 5,279,295 A | 1/1994 | Martens et al. | |
| 5,282,467 A | 2/1994 | Piantadosi et al. | |
| 5,337,745 A | 8/1994 | Benaron | |
| 5,337,937 A | 8/1994 | Remiszewski et al. | |
| 5,348,004 A | 9/1994 | Hollub | |
| 5,355,880 A | 10/1994 | Thomas et al. | |
| 5,365,066 A | 11/1994 | Krueger, Jr. et al. | |
| 5,377,674 A | 1/1995 | Kuestner | |
| 5,499,627 A | 3/1996 | Steuer et al. | |
| 5,615,689 A | 4/1997 | Kotler | |
| 5,687,721 A | 11/1997 | Kuhls | |
| 5,701,902 A * | 12/1997 | Vari et al. | 600/473 |
| 5,720,284 A | 2/1998 | Aoyagi et al. | |
| 5,735,284 A | 4/1998 | Tsoglin et al. | |
| 5,747,789 A | 5/1998 | Godik | |
| 5,755,672 A | 5/1998 | Arai et al. | |
| 5,788,643 A | 8/1998 | Feldman | |
| 5,803,908 A | 9/1998 | Steuer et al. | |
| 5,827,181 A | 10/1998 | Dias et al. | |
| 5,833,602 A | 11/1998 | Osemwota | |
| 5,853,364 A * | 12/1998 | Baker et al. | 600/300 |
| 5,860,919 A | 1/1999 | Kiani-Azarbayjany et al. | |
| 5,906,582 A | 5/1999 | Kondo et al. | |
| 6,064,898 A | 5/2000 | Aldrich | |
| 6,125,297 A | 9/2000 | Siconolfi | |
| 6,149,591 A | 11/2000 | Henderson et al. | |
| 6,178,342 B1 | 1/2001 | Thompson et al. | |
| 6,222,189 B1 | 4/2001 | Misner et al. | |
| 6,246,894 B1 | 6/2001 | Steuer et al. | |
| 6,280,381 B1 | 8/2001 | Malin et al. | |
| 6,280,396 B1 * | 8/2001 | Clark | 600/547 |
| 6,336,044 B1 | 1/2002 | Ghiassi et al. | |
| 6,370,426 B1 | 4/2002 | Campbell et al. | |
| 6,400,971 B1 | 6/2002 | Finarov et al. | |
| 6,402,690 B1 | 6/2002 | Rhee et al. | |
| 6,442,408 B1 * | 8/2002 | Wenzel et al. | 600/310 |
| 6,466,807 B1 * | 10/2002 | Dobson et al. | 600/316 |
| 6,488,677 B1 * | 12/2002 | Bowman et al. | 606/28 |
| 6,512,936 B1 * | 1/2003 | Monfre et al. | 600/322 |
| 6,591,122 B2 | 7/2003 | Schmitt | |
| 6,592,574 B1 | 7/2003 | Shimmick et al. | |
| 6,600,946 B1 | 7/2003 | Rice | |
| 6,606,509 B2 | 8/2003 | Schmitt | |
| 6,615,064 B1 * | 9/2003 | Aldrich | 600/316 |
| 6,635,491 B1 * | 10/2003 | Khalil et al. | 436/95 |
| 6,636,759 B2 * | 10/2003 | Robinson | 600/475 |
| 6,643,543 B2 | 11/2003 | Takehara et al. | |
| 6,654,620 B2 | 11/2003 | Wu et al. | |
| 6,668,181 B2 | 12/2003 | Wenzel et al. | |
| 6,675,029 B2 * | 1/2004 | Monfre et al. | 600/310 |
| 6,687,519 B2 * | 2/2004 | Steuer et al. | 600/322 |
| 6,777,240 B2 | 8/2004 | Hazen et al. | |
| 6,840,904 B2 | 1/2005 | Goldberg | |
| 6,849,046 B1 * | 2/2005 | Eyal-Bickels et al. | 600/309 |
| 6,873,865 B2 | 3/2005 | Steuer et al. | |
| 6,950,699 B1 | 9/2005 | Manwaring et al. | |
| 6,954,661 B2 | 10/2005 | Cho et al. | |
| 6,961,598 B2 | 11/2005 | Diab | |
| 7,236,811 B2 | 6/2007 | Schmitt | |
| 7,257,433 B2 | 8/2007 | Takamura et al. | |
| 7,283,242 B2 | 10/2007 | Thornton | |
| 7,398,115 B2 | 7/2008 | Lynn | |
| 2001/0020122 A1 * | 9/2001 | Steuer et al. | 600/322 |
| 2003/0060693 A1 | 3/2003 | Monfre et al. | |
| 2004/0127777 A1 | 7/2004 | Ruchti et al. | |
| 2004/0147034 A1 | 7/2004 | Gore et al. | |
| 2004/0230106 A1 | 11/2004 | Schmitt et al. | |
| 2005/0065415 A1 | 3/2005 | Cho | |
| 2005/0119538 A1 | 6/2005 | Jeon et al. | |
| 2005/0192493 A1 | 9/2005 | Wuori | |
| 2006/0020179 A1 | 1/2006 | Anderson et al. | |
| 2006/0052680 A1 | 3/2006 | Diab | |
| 2006/0122475 A1 | 6/2006 | Balberg et al. | |
| 2006/0167350 A1 | 7/2006 | Monfre et al. | |
| 2006/0247506 A1 | 11/2006 | Balberg et al. | |
| 2006/0253016 A1 | 11/2006 | Baker, Jr. et al. | |
| 2006/0276696 A1 | 12/2006 | Schurman et al. | |

FOREIGN PATENT DOCUMENTS

| | | | |
|---|---|---|---|
| EP | 1135184 A1 | 6/2000 | |
| EP | 1184663 A2 | 3/2002 | |
| EP | 1491135 | 12/2004 | |
| FR | 2710517 | 4/1995 | |
| JP | 4-40940 | 2/1992 | |
| JP | 5-329163 | 12/1993 | |
| JP | 11-244266 | 9/1999 | |
| JP | 2004081427 A | 3/2004 | |
| WO | 9519562 A | 7/1995 | |
| WO | WO 98/34097 | 8/1998 | |
| WO | WO 00/32262 A1 | 6/2000 | |
| WO | 0071025 A1 | 11/2000 | |
| WO | WO 00/71025 A1 | 11/2000 | |
| WO | WO 93/13706 A2 | 1/2001 | |
| WO | WO 01/16577 A1 | 3/2001 | |
| WO | 2003010510 A | 2/2003 | |
| WO | 2005041765 A | 5/2005 | |

OTHER PUBLICATIONS

Pace, Nello, et al., "Studies on Body Composition: III. The body water and chemically combined nitrogen content in relation to fat content," Naval Medical Research Institute, Bethesda, Maryland (Jan. 11, 1945).

Mitchell, H. M., et al., The Chemical Composition of the Adult Human Body and Its bearing on the Biochemistry of Growth), Division of Animal Nutrition, Departments of Physiology and Animal Husbandry, University of Illinois, pp. 625-637 (Feb. 1945).

Schloerb, Paul R., et al., "The Measurement of Total Body Water in the Human Subject by Deuterium Oxide Dilution," *Surgical Research Laboratories of the Peter Bent Brigham Hospital, and the Department of Surgery and the Biophysical Laboratory of the Harvard Medical School*, pp. 1296-1310 (Mar. 20, 1950).

Forbes, R.M., et al., "The Composition of the Adult Human Body as Determined by Chemical Analysis," Division of Animal Nutrition, and the Department of Anatomy, University of Illinois, Jan. 19, 1953.

Buijs, K., et al., "Near-Infrared Studies of the Structure of Water. I. Pure Water," *The Journal of Chemical Physics*, vol. 39, No. 8, pp. 2035-2041 (Oct. 15, 1963).

Choppin, G.R., et al., "Near-Infrared Studies of the Structure of Water. II. Ionic Soluation," *The Journal of Chemical Physics*, vol. 39, No. 8, pp. 2042-2050 (Oct. 15, 1963).

Goldstein, R., et al., "The Near-Infrared Absorption of Liquid Water at Temperatures Between 27 and 209° C," *J. Quant. Spectrosc. Radiat. Transfer.*, vol. 4, pp. 441-451 (1964).

Ben-Gera, I., et al., "Influence of Fat Concentration on the Absorption Spectrum of Milk in the Near-Infrared Region," *Israel J. Agile. Res.*, Vo. 18, No. 3, pp. 117-124 (Jul. 1968).

Houseman, R.A., et al., "The measurement of total body water in living pigs by deuterium oxide dilution and its relation to body composition," *Br. J. Nutr.*, vol. 30, pp. 149-156 (1973).

Krikorian, S. Edward, et al., "The identification and origin of N-H overtone and combination bands in the near-infrared spectra of simple primary and secondary amides," *Spectrochimica Acta*, vol. 29A, pp. 1233-1246 (1973).

Lesser, G.T., et al., "Body water compartments with human aging using fat-free mass as the reference standard," *Am J. Physiol Regul Integr Comp Physiol.*, vol. 236, pp. 215-220 (1979).

Sheng, Hwai-Ping, et al., "A review of body composition studies with emphasis on total body water and fat," *The American Journal of Clinical Nutrition*, vol. 32., pp. 630-647 (Mar. 1979).

Martens, H., et al., "Unscrambling Multivariate Data from Mixtures: I: Fat, water and protein determination in meat by near-infrared reflectance spectroscopy, II: soy protein and collagen determination in meat products from amino acid data," *Meat Res. Workers, Proc. European Meeting*, pp. 146-149 (1980).

Fomon, Samuel J., et al., "Body composition of reference children from birth to age 10 years," The American Journal of clinical Nutrition, vol. 35, pp. 1169-1175, (May 1982).

Lanza, Elaine, "Determination of Moisture, Protein, Fat, and Calories in Raw Pork and Beef by near Infrared Spectroscopy," *Journal of Food Science*, vol. 48, pp. 471-474 (1983).

Martens, Harald, et al., "Understanding food research data," Food Research and Data Analysis, Applied Science Publishers, pp. 5-38 (1983).

Shields, R. G., Jr., et al., "Efficacy of Deuterium Oxide to Estimate Body Composition of Growing Swine"; *Journal of Animal Science*, vol. 57, No. 1, pp. 66-73, (1983).

Wolfgang, Arneth, "Multivariate Infrared and near-infrared Spectroscopy: rapid analysis of protein, fat and water in meat," *Food Res and Data Analysis, Proc from IUoST Symp*, Oslo, Norway, pp. 239-251 (1983).

Cohn, S.H., et al., "Assessment of cellular mass and lean body mass by noninvasive nuclear techniques," *J. Lab Clin Med.*, vol. 105, pp. 305-311 (1985).

Hannon, John P., et al., "Splenic red cell sequestration and blood volume measurements in conscious pigs," *Am J. Physiol.*, vol. 248, pp. R293-R301 (1985).

Potts, R.O., et al., "A Noninvasive, in Vivo Technique to Quantitatively measure Water Concentration of the Stratum Corneum Using Attenuated Total-Reflectance Infrared Spectroscopy," *Arch. Dermatol Res.*, vol. 277, pp. 489-495 (1985).

Cox, Patrick, et al., "Variations in Lipids in Different Layers of Porcine Epidermis," *J. Invest Dermatol.*, vol. 87, pp. 741-744 (1986).

Valdes, E. V., et al., "Determination of Crude Protein and Fat in Carcass and Breast Muscle Samples of Poultry by Near Infrared Reflectance Spectroscopy," *Poultry Science*, vol. 65, pp. 485-490 (1986).

Hedberg, Chrisopher L., et al., "The Time Course of Lipid Biosynthesis in Pig Epidermis," *J. Invest Dermatol.*, vol. 91, pp. 169-174 (1988).

Hedberg, Christopher L., et al., "The nonpolar Lipids of Pig Epidermis," *J. Invest Dermatol.*, vol. 90, pp. 225-229 (1988).

Trapp, Scott A., et al., "An improved spectrophotometric bromide assay for the estimation of extracellular water volume," *Clinica Chimica Acta.*, vol. 181, pp. 207-212, (1989).

Bommannan, D., et al., "Examination of Stratum Corneum Barrier Function in Vivo by Infrared Spectroscopy," *J. Invest Dermatol*, vol. 95, pp. 403-408 (1990).

Hannon, John P., et al., "Normal pHysiological Values for Conscious Pigs Used in Biomedical Research," *Laboratory Animal Science*, vol. 40, No. 3, May 1990.

Mak, Vivien H.W., et al., "Oleic Acid Concentration and Effect in Human Stratum Corneum: Non-Invasive determination by Attenuated Total Reflectance Infrared Spectroscopy in Vivo," *Journal of Controlled Release*, vol. 12, pp. 67-75 (1990).

Edwardson, P. et al., "The Use of FT-IR for the Determination of Stratum Corneum Hydration in Vitro and in Vivo," *J. of Pharmaceutical & Biomed. Analysis*, vol. 9, Nos. 10-12, pp. 1089-10994, 1991.

Drummer, C., et al., "Effects of an acute saline infusion on fluid and electrolyte metabolism in humans," *Am J. Physiol.*, vol. 262, pp. F744-F754 (1992).

Horber, F.F., et al., "Impact of hydration status on body composition as measured by dual energy X-ray absorptiometry in normal volunteers and patients on haemodialysis," *The British Journal of Radiology*, vol. 65, pp. 895-900 (1992).

Schmitt et al., *Proc. SPIE*, "Measurement of blood hematocrit by dual-wavelength near-IP photoplethysmography," 1641:150-161 (1992).

Diaz-Carrillo, E., et al., "Near infrared calibrations for goat's milk components; protein, total casein, $\alpha_s$-, $\beta$- and $k$-caseins, fat and lactose," *J. near Infrared Spectrosc.*, vol. 1, pp. 141-146 (1993).

Martin, K., "Direct Measurement of Moisture in Skin by NIR spectroscopy," *J. Soc. Cosmet. Chem.*, 44:249-261 (1993).

Richard, Stéphanie, et al., "Characterization of the Skin in Vivo by High Resolution Magnetic Resonance Imaging: Water Behavior and Age-Related Effects," *The Journal of Investigative Dermatology*, vol. 100, No. 5, pp. 705-709 (May 1993).

Thompson et al., "Can bioelectrical impedance be used to measure total body water in dialysis patients?", *Physiol. Meas.*, 14:455-461 (1993).

Bewig, Karen M., et al., "Discriminant Analysis of Vegetable Oils by Near-Infrared Reflectance 'Spectroscopy," *JAOCS*, vol. 71, No. 2, pp. 195-200 (Feb. 1994).

Kamishikiryo-Yamashita, Hiromi, et al, "Protein Content in Milk by Near-Infrared Spectroscopy," *Journal of Food Science*, vol. 59, No. 2, pp. 313-315 (1994).

Matcher, S. J., et al., "Absolute quantification of deoxyhaemoglobin concentration in tissue near infrared spectroscopy," *Phys. Med. Biol.*, vol. 39, pp. 1295-1312 (1994).

Simanonok, Karl E., et al., "A Comprehensive Guyton Model Analysis of Physiologic Responses to Preadapting the Blood Volume as a Countermeasure to Fluid Shifts," *J. Clin Pharmacol*, vol. 34, pp. 440-453 (1994).

Steven, Alasdair C., et al., "Protein composition of cornified cell envelopes of epidermal keratinocytes," *Journal of Cell Science*, vol. 107, pp. 693-700 (1994).

Takeo, T. et al., "Skin Hydration State Estimation Using a Fiber-Optic Refractometer," *Applied Optics*, vol. 33, No. 19, Jul. 1994, p. 4267-4272.

Warren, Joan L., et al., "The burden and Outcomes Associates with Dehydration among US Elderly, 1991," *American Journal of Public Health*, vol. 84, No. 8, pp. 1265-1269 (Aug. 1994).

Åneman, Anders, et al., "Splanchnic and Renal Sympathetic Activity in Relation to Hemodynamics During Isoflurane Administration in Pigs," *Anesth Analg.*, vol. 80, pp. 135-142, (1995).

Kisch, Hille, et al., "Accuracy and reproducibility of the measurement of actively circulating blood volume with an integrated fiberoptic monitoring system," *Critical Care Medicine*, vol. 23, No. 5, pp. 885-893 (1995).

Isaksson, Tomas, et al., "Non-Destructive Determination of Fat, Moisture and Protein in Salmon Fillets by Use of Near-Infrared Diffuse Spectroscopy," *J. Sci Food Agric.*, vol. 69, pp. 95-100 (1995).

Quiniou, N., et al., "Prediction of Tissular Body Composition from Protein and Lipid Deposition in Growing Pigs," *J. Anim. Sci.*, vol. 73, pp. 1567-1575, (1995).

Avis, N. J., et al.; "In vitro multifrequency electrical impedance measurements and modeling of the cervix in late pregnancy", *Physiological Measurement*, vol. 17, pp. A97-103, 1996.

Gniadecka, M., et al., "Assessment of dermal water by high-frequency ultrasound: comparative studies with nuclear magnetic resonance," *British Journal of Dermatology*, vol. 135, pp. 218-224, (1996).

Finn, Patrick J., et al., "Progressive celluarl dehydration and proteolysis in critically ill patients," The Lancet,vol. 347, pp. 654-646 (Mar. 9, 1996).

Johnson et al., "Monitoring of Extracellular and Total Body Water during Hemodialysis Using Multifrequency Bio-Electrical Impedance Analysis," *Kidney and Blood Pressure Research*, 19:94-99 (1996).

Kotler, D.P., et al.; "Prediction of body cell mass, fat-free mass, and total body water with bioelectrical impedance analysis: effects of race, sex, and disease;" *Am J. Clin. Nutr.* 64(suppl):489S-97S (1996).

Kumar, Gitesh, et al., "Non-Invasive Optical Assessment of Tissue Hydration," *International conference on Biomedical Engineering*, Jun. 3-5 1996, Hong Kong, pp. C2-C5.

Schmitt et al., *Proc. SPIE*, "Optimum wavelengths for measurement of blood hemoglobin content and tissue hydration by NIR spectrophotometry," 2678:442-453 (1996).

De Fijter, W.M., et al., "Assessment of total body water ad lean body mass from anthropometry, Watson formula, creatinine kinetics, and body electrical impedance compared with antipyrine kinetics and peritoneal dialysis patients," *Nephrol Dial Transplant*, vol. 12, pp. 151-156 (1997).

Johansen, Lars Bo, et al., "Hemodilution, central blood volume, and renal responses after an isotonic saline infusion in humans," *Am J. Physiol.*, vol. 272, pp. R549-R556 (1997).

Visser, Marjolein, et al., "Density of fat-free body mass: relationship with race, age, and level of body fatness," *Am J. Physiol.*, vol. 272, pp. E781-E787, (1997).

Alanen, Esko, et al., "Measurement of dielectric properties of subcutaneous fat with open-ended coaxial sensors," *Phys. Med. Biol.*, vol. 43, pp. 475-485 (1998).

Alanen, Esko, et al., "Variational Formulation of Open-Ended Coaxial line in Contact with Layered Biological Medium," *IEEE Transactions on Biomedical Engineering*, vol. 45, No. 10, pp. 1241-1248 (Oct. 1998).

Bonadonna, Riccardo C., et al., "Tole of Tissue-Specific Blood Flow and Tissue Recruitment in Insulin-Mediated Glucose Uptake of Human Skeletal Muscl," *Circulation*, vol. 98, pp. 234-241, (1998).

Bracco, David, et al., "Bedside determination of fluid accumulation after cardiac surgery using segmental bioelectrical impedance," *Crit Care Med*, vol. 26, No. 6, pp. 1065-1070 (1998).

Gniadecka, Monika, et al., "Water and Protein Structure in Photoaged and Chronically Aged Skin," *J. Invest Dermatol*, vol. 111, pp. 1129-1133 (1998).

Gniadecka, Monika, et al., "Structure of Water, Proteins, and Lipids in Intact Human Skin, Hair, and Nail," *J. Invest Dermatol*, vol. 110, pp. 393-398 (1998).

Gow, Kenneth W., et al., "Effect of crystalloid administration on oxygen extraction in endotoxemic pigs," *J. Appl. Physiol.*, vol. 85, No. 5, pp. 1667-1675 (1998).

Husby, P., et al., "Midazolam-fentanyl-isoflurane anaesthesia is suitable for haemodynamic and fluid balance studies in pigs," *Laboratory Animals*, vol. 32, pp. 316-323 (1998).

Mitchell, A. D., et al., "Composition Analysis of Pork Carcasses by Dual-Energy X-Ray Absorptiometry," *J. Anim. Sci.*, vol. 76, pp. 2104-2114 (1998).

Mahan, D. C., et al., "Essential and Nonessential Amino Acid Composition of Pigs from Birth to 145 Kilograms of Body Weight, and Comparison to Other Studies," *J. Anim. Sci.*, vol. 76, pp. 513-521, (1998).

Martin, Kathleen, "In Vivo Measurements of Water in Skin by Near-Infrared Reflectance," *Applied Spectroscopy*, vol. 52, No. 7, 1998, pp. 1001-1007.

Schou, Henning, et al., "Uncompensated Blood Los is not Tolerated During Acute Normovolemic Hemodilution in Anesthetized Pigs," *Anesth Analg.*, vol. 87, pp. 786-794 (1998).

Stranc, M.F., et al., "Assessment of tissue viability using near-infrared spectroscopy," *British Journal of Plastic Surgery*, vol. 51, pp. 210-217, (1998).

Thomas, B. J., et al., "Bioimpedance Spectrometry in the Determination of Body Water Compartments: Accuracy and Clinical Significance," *Appl. Radiat. Isot.*, vol. 49, No. 5/6, pp. 447-455, (1998).

Wilhelm, K.P., "Possible Pitfalls in Hydration Measurements," *Skin Bioengineering Techniques and Applications in Dermatology and Cosmetology*, vol. 26, pp. 223-234 (1998).

Vrhovski, Bernadette, et al., "Biochemistry of tropoelastin," *Eur. J. Biochem.*, vol. 258, pp. 1-18 (1998).

Alanen, Esko, et al., "Penetration of electromagnetic fields of an open-ended coaxial probe between 1 MHz and 1 GHz in dielectric skin measurements," *Phys. Med. Biol.*, vol. 44, pp. N169-N176 (1999).

Dickens, Brian, et al., "Estimation of Concentration and Bonding Environment of Water Dissolved in Common Solvents Using Near Infrared Absorptivity," *J. Res. Natl. Inst. Stand. Technol.*, vol. 104, No. 2, pp. 173-183 (Mar.-Apr. 1999).

Fornetti, Willa C., et al., "Reliability and validity of body composition measures in female athletes," *Journal of Applied Physiology*, vol. 87, pp. 1114-1122, (1999).

Fusch, Christoph, et al., "Neonatal Body COmposition: Dual-Energy X-Ray Absorptiometry, Magnetic Resonance Imaging, and Three-Dimensional Chemical Shift Imaging versus Chemical Analysis in Piglets," *Pediatric Research*, vol. 46, No. 4, pp. 465-473 (1999).

Gudivaka, R., et al., "Single- and multifrequency models for bioelectrical impedance analysis of body water compartments," *J. Appl. Physiol.*, vol. 87, No. 3, pp. 1087-1096 (1999).

Jennings, Graham, et al., "The Use of infrared Spectrophotometry for Measuring Body Water Spaces," vol. 45, No. 7, pp. 1077-1081 (1999).

Kalantar-Zadeh, Kamyar, et al., "Near infra-red interactance for nutritional assessment of dialysis patients," *Nephrol Dial Transplant*, vol. 14, pp. 169-175 (1999).

Kayser-Jones, Jeanie, et al., "Factors Contributing to Dehydration in Nursing Homes: Inadequate Staffing and Lack of Professional Supervision," *J. Am Geriatr. Soc.*, vol. 47, pp. 1187-1194 (1999).

Lange, Neale R., et al., "The measurement of lung water, " *Critical Care*, vol. 3, pp. R19-R24 (1999).

Marken Lichtenbelt, Wouter D. Van, et al., "Increased extracellular water compartment, relative to intracellular water compartment, after weight reduction," *Journal of Applied Physiology*, vol. 87, pp. 294-298 (1999).

Rennie, Michael J., "Perspectives—Teasing out the truth about collagen," *Journal of Physiology*, vol. 521, p. 1 (1999).

Sowa et al., "New-infrared spectroscopic assessment of tissue hydration following surgery", *Journal of Surgical Research*, 86:62-69 (1999).

Wagner, J.R., et al., "Analysis of Body Composition Changes of Swine During Growth and Development," *J. Anim. Sci.*, vol. 77, pp. 1442-1466 (1999).

Wang, Zimian, et al., "Hydration of fat-free body mass: new physiological modeling approach," *Am. J. Physiol.*, vol. 276, pp. E995-E1003 (1999).

Wang, Zimian, et al., "Hydration of fat-free body mass: review and critique of a classic body-composition constant," *Am J. Clin. Nutr.*, vol. 69, pp. 833-841 (1999).

Ward, L., et al., "Multiple frequency bioelectrical impedance analysis: a cross-validation study of the inductor circuit and Cole models," *Physiol. Meas.*, vol. 20, pp. 333-347 (1999).

Well, Jonathan CK, et al., "Four-component model of body composition in children: density and hydration of fat-free mass and comparison with simpler models," *Am J. Clin. Nutr.*, vol. 69, pp. 904-912 (1999).

Butte, Nancy F., et al., "Body Composition during the First 2 Years of Life; An Updated Reference," *Pediatric Research*, vol. 47, No. 5, pp. 578-585 (2000).

Feigenbaum, Matthew S., et al., "Contracted Plasma and Blood Volume in Chronic Heart Failure," *J Am Coll. Cardiol.*, vol. 35, No. 1, pp. 51-55 (Jan. 2000).

Kays, Sandra E., et al., "Predicting protein content by near infrared reflectance spectroscopy in diverse cereal food products," *J. Near Infrared Spectrosc.*, vol. 8, pp. 35-43 (2000).

Lucassen, G., et al., "Water Content and Water Profiles in Skin Measured by FTIR and Raman Spectroscopy," *Proc. SPIE*, vol. 4162, pp. 39-45 (2000).

Plank, L. D., et al., "Similarity of Changes in Body Composition in Intensive Care Patients following Severe Sepsis or Major Blunt Injury," *Annals New York Academy of Sciences*, pp. 592-602 (2000).

Ritz, P., et al., "Body Water Spaces and Cellular Hydration during Healthy Aging," *Annals New York Academy of Sciences*, pp. 474-483 (2000).

Schoeller, Dale, "Bioelectrical Impedance Analysis—What does it measure?" *Annals New York Academy of Sciences*, pp. 159-162 (2000).

Starcher, Barry C., "Lung Elastin and Matrix," *Chest*, vol. 117, No. 5, pp. 229S-234S, May 2000 Supplement.

Young, A.E.R., et al., "Behaviour of near-infrared light in the adult human head: implications of clinical near-infrared spectroscopy," *British Journal of Anaesthesia*, vol. 84, No. 1, pp. 38-42 (2000).

Zembrzuski, Cora, "Nutrition and Hydration," Best Practices in Nursing Care to Older Adults, The Hartford Institute for Geriatric Nursing, vol. 2, No. 2, Sep. 2000, 2 pages.

Attas, Michael, et al., "Visualization of cutaneous hemoglobin oxygenation and skin hydration using near-infrared spectroscopic imaging," *Skin Research and Technology*, vol. 7, pp. 238-245, (2001).

Bray, George A., et al., "Evaluation of body fat in fatter and leaner 10-y-old African American and white children: the Baton Rouge Children's Study," *Am J. Clin Nutr*, vol. 73, pp. 687-702 (2001).
Campbell, Wayne W., et al., "The Recommended Dietary Allowance for Protein May Not Be Adequate for Older People to Maintain Skeletal Muscle," *Journal of Gerontology*, vol. 56A, No. 6, pp. M373-M380 (2001).
Divert, Victor E., "Body Thermal State Influence on Local Skin Thermosensitivity," *International Journal of Circumpolar Health*, vol. 60, pp. 305-311 (2001).
Du, Y., et al., "Optical properties of porcine skin dermis between 900 nm and 1500 nm," *Phys. Med. Biol.*, vol. 46, pp. 167-181 (2001).
Endo, Yutaka, et al., "Water drinking causes a biphasic change in blood composition in humans," *Pflügers Arch—Eur J. Physiol*, vol. 442, pp. 362-368 (2001).
Garaulet, Marta, et al., "Site-specific differences in the fatty acid composition of abdominal adipose tissue in an obese population from a Mediterranean area: relation with dietary fatty acids, plasma lipid profile, serum insulin, and central obesity," *Am J. Clin. Nutr.*, vol. 74, pp. 585-591 (2001).
Haga, Henning A., et al., "Electroencephalographic and cardiovascular indicators of nociception during isoflurane anaesthesia in pigs," *Veterinary Anaesthesia and Analgesia*, vol. 28, pp. 126-131 (2001).
Kalantar-Zadeh, Kamyar, et al., "Near infra-red interactactance for Longitudinal Assessment of Nutrition in Dialysis Patients," *Journal of Renal Nutrition*, vol. 11, No. 1, pp. 23-31 (Jan. 2001).
Kamba, Masayuki, et al., "Proton magnetic resonance spectroscopy for assessment of human body composition," *Am J. Clin. Nutr.*, vol. 73, pp. 172-176 (2001).
Lever, M., et al., "Some ways of looking at compensatory kosmotropes and different water environments," *Comparative Biochemistry and Physiolog.*, vol. 130, Part A, pp. 471-486, (2001).
Mingrone, G., et al., "Unreliable use of standard muscle hydration value in obesity," *Am J. Physiol Endocrinal Metab.*, vol. 280, pp. E365-E371, (2001).
Šašic, Slobodan, et al., "Short-Wave Near-Infrared Spectroscopy of Biological Fluids. 1. Quantitative Analysis of Fat, Protein, and Lactose in Raw Milk by Partial Least-Squares Regression and Band Assignment," *Anal. Chem.*, vol. 73, pp. 64-71 (2001).
Schnickel, A.P., et al., "Evaluation of alternative measures of pork carcass composition," *J. Anim. Sci.*, vol. 79, pp. 1093-1119, (2001).
Sowa et al., "Near infrared spectroscopic assessment of hemodynamic changes in the early post-burn period," *Burns*, 27(3):241-9 (2001).
Troy, Tamara L., et al., "Optical properties of human skin in the near infrared wavelength range of 1000 to 2200nm," *Journal of Biomedical Optics*, vol. 6, No. 2, pp. 167-176 (Apr. 2001).
Tsukahara, K., et al., "Dermal fluid translocation is an important determinant of the diurnal variation in human skin thickness," *British Journal of Dermatology*, vol. 145, pp. 590-596 (2001).
Vescovi, Jason D., et al., "Evaluation of the BOD POD for estimating percentage body fat in a heterogeneous group of adult humans," *Eur J. Appl. Physiol.*, vol. 85, pp. 326-332 (2001).
Wang, Zimian, et al., "Magnitude and variation of ratio of total body potassium to fat-free mass: a cellular level modeling study," *Am J. Physiol. Endocrinal. Metab.*, vol. 281, pp. E1-E7, (2001).
Watson, Walter, "Hydration of fat-free body mass: new physiological modeling approach," *Am J. Physiol. Endocrinol. Metab.*, Letters to the Editor, vol. 278, pp. E752-E753 (2001).
Attas, E. Michael, et al., "Near-IR Spectroscopic Imaging for Skin Hydration: The Long and the Short of It," *Biopolymers*, vol. 67, No. 2, pp. 96-106 (2002).
Attas, M. et al., "Long-Wavelength Near-Infrared Spectroscopic Imaging for in-Vivo Skin Hydration Measurements," *Vibrational spectroscopy* (Feb. 28, 2002), vol. 28, No. 1, p. 37-43.
Blank, T.B., et al., "Clinical Results from a Non-Invasive Blood Glucose Monitor," *Photonics West 2002 Meeting*, San Jose, California, Jan. 19-25, 2002 (25 pages).
Chamney, Paul W., et al., "A new technique for establishing dry weight in hemodialysis patients via whole body bioimpedance," *Kidney International*, vol. 61, pp. 2250-2258 (2002).

Drobin, Dan, et al., "Kinetics of Isotonic and Hypertonic Plasma vol. Expanders," *Anesthesiology*, vol. 96, No. 6, pp. 1371-1380 (Jun. 2002).
Endo, Yutaka, et al., "Changes in Blood Pressure and Muscle Sympathetic Nerve Activity during Water Drinking in Humans," *Japanese Journal of Physiology*, vol. 52, pp. 421-427 (2002).
Haga, Henning A., et al., "Motor responses to stimulation during isoflurane anaesthesia in pigs," *Veterinary Anaesthesia and Analgesia*, vol. 29, pp. 69-75 (2002).
Klaus, Stephan, et al., "Assessment of fluid balance by measurement of skin tissue thickness during clinical anaesthesia," *Clin. Physiol. & Func. Im.*, vol. 22, pp. 197-201 (2002).
Meglinski, Igor V., et al., "Quantitative assessment of skin layers absorption and skin reflectance spectra simulation in the visible and near-infrared spectral regions," *Physiol. Meas.*, vol. 23, pp. 741-753, (2002).
Perez-de-Sá, Valeriá, et al., "Mild Hypothermia Has Minimal Effects on the Tolerance to Severe Progressive Normovolemic Anemia in Swine," *Anesthesiology*, Vo. 97, pp. 1189-1197 (2002).
Ponec, Maria, et al., "Charactrization of Reconstructed Skin Models," *Skin Pharmacol Appl Skin Physiol.*, vol. 15, Supplement 1, pp. 4-17, (2002).
Querleux, B., et al., "Anatomy and physiology of subcutaneous adipose tissue by in vivo magnetic resonance imaging and spectroscopy: Relationships with sex and presence of cellulite," *Skin Research and Technology*, vol. 8, pp. 118-124 (2002).
Van Bommel, Jasper, et al., "Intestinal and Cerebral Oxygenation during Severe Isovolemic Hemodilution and Subsequent Hyperoxic Ventilation in a Pig Model," *Anesthesiology*, vol. 97, No. 3, pp. 660-670 (Sep. 2002).
Wong, William W., et al., "Evaluating body fat in girls and female adolescents: advantages and disadvantages of dual-energy X-ray absorptiometry," *Am J. Clin Nutr.*, vol. 76, pp. 384-389 (2002).
Baković, Darija, et al., "Spleen volume and blood flow response to repeated breath-hold apneas," *J. Appl. Physiol.*, vol. 95, pp. 1460-1466 (2003).
Bartok, Cynthia, et al., "Measurement of nutritional statusin simulated microgravity by bioelectrical impedance spectroscopy," *J. Appl. Physiol.*, vol. 95, pp. 225-232 (2003).
Bouwstra, Joke A., et al., "Water Distribution and Related Morphology in Human Stratum Corneum at Different Hydration Levels," *J. Invest Dermatol*, vol. 150, pp. 750-758 (2003).
Butte, Nancy F., et al., "Composition of gestational weight gain impacts maternal fat retention and infant birth weight," *Am J. Obstet Gynecol*, vol. 189, pp. 1423-1432 (2003).
Cloonan, Clifford C., "Don't Just Do Something, Stand There!: To Teach of not to Teach, That is the Question—Intravenous Fluid Resuscitation Training for Combat Lifesavers," *The Journal of Trauma, Injury, Infection, and Critical Care*, vol. 54, No. 5, pp. S20-S25 (May Supplement 2003).
Cook, Lynda S., "IV Vluid Resuscitation," *Journal of Infusion Nursing*, vol. 26, No. 5, pp. 296-303 (Sep./Oct. 2003).
Dey, D.K., et al., "Body composition estimated by bioelectric impedance in the Swedish elderly. Development of population-based prediction equation and reference values of fat-free mass and body fat for 70- and 75-y olds," *European Journal of Clinical Nutrition*, vol. 57, pp. 909-916 (2003).
Farstad, M., et al., "Fluid extravasation during cardiopulmonary bypass in piglets—effects of hypothermia and different cooling protocols," *Acta Anaesthesiol. Scand.*, vol. 47, pp. 397-406 (2003).
Grandjean et al., "Hydration: issues for the $21^{st}$ century", *Nutrition Reviews*, 61(8):261-271 (2003).
Heise, H.M., et al., "Reflectance spectroscopy can quantify cutaneous haemoglobin oxygenation by oxygen uptake from the atmosphere after epidermal barrier distruption," *Skin Research and Technology*, vol. 9, pp. 295-298 (2003).
Kasemsumran, Sumaporn, et al., "Simultaneous determination of human serum albumin, γ-globulin, and glucose in a phosphate buffer solution by near-infrared spectroscopy with moving window partial least-squares regression," *Analyst*, vol. 128, pp.-1471-1477 (2003).
Kemming, G.I., et al., "Hyperoxic ventilation at the critical haematocrit," *Resuscitation*, vol. 56, pp. 289-297 (2003).

Kurita, T., et al., "Comparison of isoflurane and propofol-fentanyl anaesthesia in a swine model of asphyxia," *British Journal of Anaesthesia*, vol. 91, No. 6, pp. 871-877 (2003).

Laaksonen, DE, et al., "Changes in abdominal subcutaneous fat water content with rapid weight loss and long-term weight maintenance in abdominally obese men and women," *International Journal of Obesity*, vol. 27, pp. 677-683 (2003).

Mao, Jinshu, et al., "Study of Novel Chitosan-gelatin artificial skin in vitro," *J. Miomed Mater Res.*, vol. 64, Part A, pp. 301-308 (2003).

Mauran, P., et al., "Renal and hormonal responses to isotonic saline infusion after 3 days' dead-down tilt vs. supine and seated positions," *Acta Physiol. Scand.*, vol. 177, pp. 167-176, (2003).

McHugh, Gerard, "Letter—Passive leg elevation and head-down tilt: effects and duration of changes," *Critical Care*, vol. 7, No. 3, p. 246 (Jun. 2003).

Meglinski, I.V., et al., "Computer simulation of the skin reflectance spectra," *Computer Methods and Programs in Biomedicine*, vol. 70, pp. 179-186, (2003).

Mendelsohn, Richard, et al., "Infrared microspectroscopic imaging maps the spatial distribution of exogenous molecules in skin," *Journal of Biomedical Optics*, vol. 8, No. 2, ppl 185-190 (Apr. 2003).

Mentes, Janet C., et al., "Reducing Hydration=-Linked events in Nursing Home Residents," *Clinical Nursing Research*, vol. 12, No. 3, pp. 210-225 (Aug. 2003).

Merritt, Sean, et al., "Coregistration of diffuse optical spectroscopy and magnetic resonance imaging in a rat tumor model," *Applied Optics*, vol. 42, No. 16, pp. 2951-2959 (Jun. 2003).

Parker, Lisa, et al., "Validity of Six Field and Laboratory Methods for Measurement of Body Composition in Boys," *Obesity Research*, vol. 11, No. 7, pp. 852-858 (Jul. 2003).

Petäjä L., et al., "Dielectric constant of skin and subcutaneous fat to assess fluid changes after cardiac surgery", *Physiological Measurement*, 24: 3383-390, 2003.

Richardson, Andrew D., et al., "Multivariate analyses of visible/near infrared (VIS/NIR) absorbance spectra reveal underlying spectral differences among dried, ground confer needle samples from different growth environments," *New Phytologist*, vol. 161, pp. 291-301 (2003).

Robinson, Martin P., et al., "A novel method of studying total body water content using a resonant cavity: experiments and numerical simulation," Phys. Med. Biol., vol. 48, pp. 113-125, (2003).

Sergi, Giuseppe, et al., "Changes in Fluid Compartments and Body Composition in Obese Women after Weight Loss Induced by Gastric Banding," *Ann. Nutr Metab.*, vol. 47., pp. 152-157 (2003).

Wang, Zimian, et al., "Magnitude and variation of fat-free mass density: a cellular level body composition modeling study," *Am J. Physiol. Endocrinal. Metab.*, vol. 284, pp. E267-E273 (2003).

Windberger, U, et al., "Whole bloOd viscosity, plasma viscosity and erythrocyte aggregation in nine mammalian species; reference values and comparison of data," *Exp., Physiol.*, vol. 88, No. 3, pp. 431-440 (2003).

Wolf, Martin, et al., "Absolute Frequency-Domain pulse Oximetry of the Brain: Methodology and Measurements," *Oxygen Transport to Tissue XXIV*, Chapter 7, Dunn and Swartz, Kluwer Academic/Plenum Publishers, pp. 61-73 (2003).

Garcia-Olmo, J., et al., "Advantages and disadvantages of multiple linear regression and partial least squares regression equations for the prediction of fatty acids," pp. 253-258 (undated).

Wang, Zimian, et al., "Cellular-Level Body Composition Model—A New Approach to Studying Fat-free Mass Hydration," *Annals New York Academy of Sciencei*, pp. 306-311 (undated).

Ritz, Patrick, "Chronic Cellular Dehydration in the Aged Patient," Journal of Gerontology, vol. 56A, No. 6, pp. M349-M352 (2001).

J. H. Ali, et al.; "Near Infrared Spectroscopy and Imaging to Prove differences in Water content in normal and Cancer Human Prostate Tissues," Technology in Cancer Research & Treatment, vol. 3, No. 5, Oct. 2004; pp. 491-497.

Arimoto et al., "Non-contact skin moisture measurement based on near-infrared spectroscopy", Applied Spectroscopy, 58(12):1439-1445 (2004).

Ritz, P., et al., "Body Water Spaces and Cellular Hydration during Healthy Aging," Annals New York Academy of Sciences, pp. 474-483 (2000).

* cited by examiner

DEVICE AND METHOD FOR MONITORING BODY FLUID AND ELECTROLYTE DISORDERS

CROSS-REFERENCES TO RELATED APPLICATIONS

This application is a continuation of U.S. patent application Ser. No. 10/699,610, filed on Oct. 30, 2003, which is a continuation-in-part of U.S. patent application Ser. No. 10/441,943, filed on May 20, 2003, which is a continuation of U.S. patent application Ser. No. 09/810,918, filed on Mar. 16, 2001, now U.S. Pat. No. 6,591,122, the full disclosures of which are incorporated herein by reference.

BACKGROUND

The maintenance of body fluid balance is of foremost concern in the care and treatment of critically ill patients, yet physicians have access to few diagnostic tools to assist them in this vital task. Patients with congestive heart failure, for example, frequently suffer from chronic systemic edema, which must be controlled within tight limits to ensure adequate tissue perfusion and prevent dangerous electrolyte disturbances. Dehydration of infants and children suffering from diarrhea can be life-threatening if not recognized and treated promptly.

The most common method for judging the severity of edema or dehydration is based on the interpretation of subjective clinical signs (e.g., swelling of limbs, dry mucous membranes), with additional information provided by measurements of the frequency of urination, heart rate, serum urea nitrogen SUN/creatinine ratios, and blood electrolyte levels. None of these variables alone, however, is a direct and quantitative measure of water retention or loss.

The indicator-dilution technique, which provides the most accurate direct measure of water in body tissues, is the present de facto standard for assessment of body fluid distribution. It is, however, an invasive technique that requires blood sampling. Additionally, a number of patents have disclosed designs of electrical impedance monitors for measurement of total body water. The electrical-impedance technique is based on measuring changes in the high-frequency (typically 10 KHz-1 MHz) electrical impedance of a portion of the body. Mixed results have been obtained with the electrical-impedance technique in clinical studies of body fluid disturbances as reported by various investigators. The rather poor accuracy of the technique seen in many studies points to unresolved deficiencies of these designs when applied in a clinical setting.

Therefore, there exists a need for methods and devices for monitoring body water fractions which do not suffer from problems due to their being invasive, subjective, inaccurate, and difficult to interpret for the purpose of clinical diagnosis and intervention.

SUMMARY

Embodiments of the present invention provide devices and methods that measure body fluid-related metrics using spectrophotometry that may be used to facilitate diagnosis and therapeutic interventions aimed at restoring body fluid balance. The disclosed invention facilitates rapid, non-invasive, and continuous measurement of fractional tissue water, $f_w$. Additional embodiments facilitate intermittent measurement of $f_w$. The specifications of source-detector spacings, wavelength ranges of optical measurement, and algorithms for combining the measurements, provide highly accurate and reproducible methods for determination of $f_w$.

In one embodiment, the present invention provides a device for measuring a body-tissue water content metric as a fraction of the fat-free tissue content of a patient using optical spectrophotometry. The device includes a probe housing configured to be placed near a tissue location which is being monitored; light emission optics connected to the housing and configured to direct radiation at the tissue location; light detection optics connected to the housing and configured to receive radiation from the tissue location; and a processing device configured to process radiation from the light emission optics and the light detection optics to compute the metric where the metric includes a ratio of the water content of a portion of patient's tissue in relation to the lean or fat-free content of a portion of patient's tissue.

In another embodiment, the present invention provides a device for measuring a body-tissue metric using optical spectrophotometry. The device includes a probe housing configured to be placed near a tissue location which is being monitored; light emission optics connected to the housing and configured to direct radiation at the tissue location; light detection optics connected to the housing and configured to receive radiation from the tissue location; and a processing device configured to process radiation from the light emission optics and the light detection optics to compute the metric where the body tissue metric includes a quantified measure of a ratio of a difference between the water fraction in the blood and the water fraction in the extravascular tissue over the fractional volume concentration of hemoglobin in the blood.

In another aspect, the present invention provides a method for measuring a body-tissue water content metric in a human tissue location as a fraction of the fat-free tissue content of a patient using optical spectrophotometry. The method includes placing a probe housing near the tissue location; emitting radiation at the tissue location using light emission optics that are configured to direct radiation at the tissue location. The method also includes detecting radiation using light detection optics that are configured to receive radiation from the tissue location; and processing the radiation from the light emission optics and the light detection optics; and computing the water content metric, where the water content metric, $f_w^l$ is determined such that $$f_w^l = \frac{\left[\sum_{n=1}^{N} p_n \log\{R(\lambda_n)\}\right] - \left[\sum_{n=1}^{N} p_n\right] \log\{R(\lambda_{N+1})\}}{\left[\sum_{m=1}^{M} q_m \log\{R(\lambda_m)\}\right] - \left[\sum_{m=1}^{M} q_m\right] \log\{R(\lambda_{M+1})\}},$$

and where:
$p_n$ and $q_m$ are calibration coefficients;
$R(\lambda)$ is a measure of a received radiation at a wavelength;
n=1–N and m=1–M represent indexes for a plurality of wavelengths which may consist of the same or different combinations of wavelengths. The method may also include displaying the volume fraction of water on a display device.

In another embodiment, the present invention provides a method for measuring a body-tissue metric in a human tissue location using optical spectrophotometry. The method includes emitting and detecting radiation using light emission and detection optics. In addition, the method includes processing the radiation from light emission and detection optics to compute the metric where the body fluid-related metric is related to a quantified measure of a ratio of a difference between the water fraction in the blood and the water fraction in the extravascular tissue over the fractional volume concentration of hemoglobin in the blood. In one aspect, the metric is a water balance index Q, such that:

$$Q = \frac{f_w^{IV} - f_w^{EV}}{f_h^{IV}} = a_1 \frac{(\Delta R/R)_{\lambda_1}}{(\Delta R/R)_{\lambda_2}} + a_0$$

where $f_w^{IV}$ and $f_w^{EV}$ are the fractional volume concentrations of water in blood and tissue, respectively, $f_h^{IV}$ is the fractional volume concentration of hemoglobin in the blood, $(\Delta R/R)_\lambda$ is the fractional change in reflectance at wavelength $\lambda$, due to a blood volume change in the tissue, and $\alpha_o$ and $\alpha_1$ are calibration coefficients.

In another embodiment, the present invention provides a method for measuring a physiological parameter in a human tissue location. The method includes emitting radiation at the tissue location using light emission optics and detecting radiation using light detection optics. Furthermore, the method includes processing the radiation from the light emission optics and the light detection optics and computing the physiological parameter, where the parameter is determined such that it is equal to $$\frac{\left[\sum_{n=1}^{N} p_n \log\{R(\lambda_n)\}\right] - \left[\sum_{n=1}^{N} p_n\right] \log\{R(\lambda_{N+1})\}}{\left[\sum_{m=1}^{M} q_m \log\{R(\lambda_m)\}\right] - \left[\sum_{m=1}^{M} q_m\right] \log\{R(\lambda_{M+1})\}},$$

and where:
$p_n$ and $q_m$ are calibration coefficients; $R(\lambda)$ is a measure of a received radiation at a wavelength; n=1–N and m=1–M represent indexes for a plurality of wavelengths which may be the same or different combinations of wavelengths. In one aspect, the physiological parameter is a an oxygen saturation values. In another aspect, the physiological parameter is a fractional hemoglobin concentration.

In yet another embodiment, the present invention provides a method of assessing changes in volume and osmolarity of body fluids near a tissue location. The method includes emitting radiation at a tissue location using light emission optics and detecting radiation using light detection optics that are configured to receive radiation from the tissue location. The method also includes processing the radiation from the light emission optics and the light detection optics; determining a water balance index using the processed radiation; determining a tissue water concentration and analyzing in combination the water balance index and the tissue water concentration to assess changes in volume and osmolarity of body fluids near the tissue location.

For a fuller understanding of the nature and advantages of the embodiments of the present invention, reference should be made to the following detailed description taken in conjunction with the accompanying drawings.

DETAILED DESCRIPTION

Figure 1:
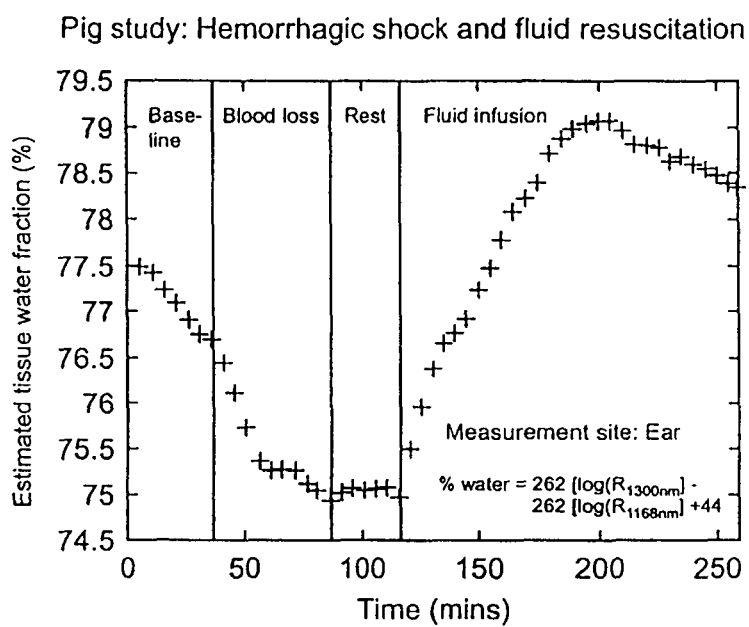
FIG. 1 is a graph showing tissue water fraction measured on the ear of a pig during an experiment using reflectance measurements at two wavelengths.

Embodiments of the present invention overcome the problems of invasiveness, subjectivity, inaccuracy, and difficulty of interpretation for the purpose of clinical diagnosis and intervention, from which previous methods for body fluid assessment have suffered. The method of diffuse reflectance near-infrared ("NIR") spectroscopy is employed to measure the fraction of water in skin. An increase or decrease in the water content of the skin produces unique alterations of its NIR reflectance spectrum in three primary bands of wavelengths (950-1400 nm, 1500-1800 nm, and 2000-2300 nm) in which none-heme proteins (primarily collagen and elastin), lipids, hemoglobin, and water absorb. According to the results of numerical simulations and experimental studies carried out by the inventors, the tissue water fraction, $f_w$, defined spectroscopically as the ratio of the absorbance of water and the sum of the absorbances of water and other constituents of the tissue, can be measured accurately in the presence of nonspecific scattering variation, temperature, and other interfering variables.

Various constituents of tissue, other than water, are included in the denominator of the ratio used to compute the tissue water fraction according to the embodiments of the present invention. In one embodiment, all of the other major tissue constituents, such as non-heme protein, lipid ("fat"), and hemoglobin, are included, resulting in the computation of the total tissue water fraction, $f_w^T$. In other embodiments, certain constituents of the tissue are specifically excluded from the measured tissue water fraction. Spectroscopic methods for the removal of certain tissue constituents from the computation of tissue water fraction are disclosed, either by choosing spectral regions where the absorbance contribution due to these tissue constituents is small, or by appropriately combining spectroscopic measurements made at multiple wavelengths to cancel the absorbance contribution due to these tissue constituents. The use of such spectroscopic methods for removing the absorbance contribution due to lipid from the measurement, thereby providing fractional water in fat-free or lean tissue, $f_w^l$, are described. Spectroscopic methods for the exclusion of hemoglobin from the fractional water measurement are also disclosed.

In addition to these spectroscopic methods, physical methods for including and excluding certain tissue constituents are also described in the present invention. By disclosing source-detector separations in the range of 1-5 mm, the present invention targets the dermis, simultaneously avoiding shallow penetration that would be indicative only of the outer dead layer of the skin as well as avoiding deep penetration into the underlying, high fat-content layer, or even further into bone-containing layers. Additional disclosures include the application of pressure at the tissue site of the optical measurement allowing various mobile constituents of the tissue to be included or excluded from the fractional water measurement. In one embodiment, the fractional water is measured before and after the application of pressure at the tissue site, allowing the mobile intravascular portion of the tissue to be included or excluded from the measurement. By this means, measurements of the fractional water content in the intravascular space, $f_w^{IV}$, extravascular space, $f_w^{EV}$, and a difference between the two $f_w^{IV}-f_w^{EV}$, is accomplished. In additional embodiments, these measurements are accomplished by photoplethysmography, taking advantage of the natural arterial pulsation of blood through tissue.

In the following detailed descriptions of the embodiments of the invention, the terms "fractional tissue water", "tissue water fraction", "water fraction", and "$f_w$" all have equivalent meanings and are meant as general terms that include all of the more specific measurements outlined above, including, but not limited to, total tissue water fraction ($f_w^T$), lean tissue water fraction ($f_w^l$), intravascular water fraction ($f_w^{EV}$), and extravascular water fraction ($f_w^{EV}$).

In embodiments of the present invention, the apparatus and its associated measurement algorithm are designed according to the following guidelines:

1. To avoid the shunting of light through the superficial layers of the epidermis, the light source and detector in optical reflectance probe have low numerical apertures, typically less than 0.3.
2. The spacing between the source and detector in the probe is in the range of 1-5 mm to confine the light primarily to the dermis.
3. The reflectances are measured at wavelengths greater than approximately 1150 nm to reduce the influence of hemoglobin absorption. Alternatively, reflectances are measured at wavelengths as short as 950 nm, but the influence of hemoglobin absorbance is reduced by appropriately combining measurements of reflectance at multiple wavelengths. Or as a further alternative, the absorbance of hemoglobin is intentionally included in the denominator of the ratio used to compute tissue water fraction.
4. To ensure that the expression that relates the measured reflectances and water content yields estimates of water fraction that are insensitive to scattering variations, the lengths of the optical paths through the dermis at the wavelengths at which the reflectances are measured are matched as closely as possible. This matching is achieved by judicious selection of wavelength sets that have similar water absorption characteristics. Such wavelength sets may be selected from any one of the three primary wavelength bands (950-1400 nm, 1500-1800 nm, and 2000-2300 nm) discussed above. Wavelength pairs or sets are chosen from within one of these three primary bands, and not from across the bands. More particularly the wavelength pair of 1180 and 1300 nm is one such wavelength set where the lengths of the optical paths through the dermis at these wavelengths are matched as closely as possible.
5. To ensure that the expression that relates the measured reflectances and water fractions yields estimates of water fraction that are insensitive to temperature variations, the wavelengths at which the reflectances are measured are chosen to be either close to temperature isosbestic wavelengths in the water absorption spectrum or the reflectances are combined in a way that cancels the temperature dependencies of the individual reflectances. Typically, absorption peaks of various biological tissue constituents may shift with variations in temperature. Here, wavelengths are selected at points in the absorption spectrum where no significant temperature shift occurs. Alternately, by knowing the value of this temperature shift, wavelength sets may be chosen such that any temperature shift is mathematically canceled out when optical measurements are combined to compute the value of a tissue water metric. Such wavelength sets may be selected from any one of the three primary wavelength bands (950-1400 nm, 1500-1800 nm, and 2000-2300 nm) discussed above. Wavelength pairs or sets are chosen from within one of these three primary bands, and not from across the bands. More particularly the wavelength pair of 1180 and 1300 nm are one such pair of temperature isosbestic wavelengths in the water absorption spectrum.
6. The reflectances measured at two or more wavelengths are combined to form either a single ratio, a sum of ratios, a ratio of ratios of the form log [$R(\lambda_1)/R(\lambda_2)$], or a ratio of weighted sums of log [$R(\lambda)$] terms, in which the numerator depends primarily on the absorbance of water and the denominator depends primarily on the sum of the volume fractions of water and other specific tissue constituents, such that the denominator is equally sensitive to a change in the concentration of any of these specific constituents and water.

Thus, in one embodiment of the present invention the water fraction, $f_w$ is estimated according to the following equation, based on the measurement of reflectances, $R(\lambda)$ at two wavelengths and the empirically chosen calibration constants $c_0$ and $c_1$:

$$f_w = c_1 \log [R(\lambda_1)/R(\lambda_2)] + c_0 \qquad (1)$$

Numerical simulations and in vitro experiments indicate that the total tissue water fraction, $f_w^T$, can be estimated with an accuracy of approximately +/-2% over a range of water contents between 50 and 80% using Equation (1), with reflectances $R(\lambda)$ measured at two wavelengths and the calibration constants $c_0$ and $c_1$ chosen empirically. Examples of suitable wavelength pairs are $\lambda_1=1300$ nm, $\lambda_2=1168$ nm, and $\lambda_1=1230$ nm, $\lambda_2=1168$ nm.

The ability to measure changes in the total tissue water content in the ear of a pig using two-wavelength NIR reflectometry was demonstrated experimentally in a study in which a massive hemorrhage was induced in a pig and the lost blood was replaced with lactated Ringer's solution over a period of several hours. Ringer's solution is a well-known solution of salts in boiled and purified water. FIG. 1 shows the total water fraction in the skin of the ear of a pig, measured using Equation (1) with $\lambda_1=1300$ nm and $\lambda_2=1168$ nm. Referring to FIG. 1, it should be noted that experimental observations of concern to this embodiment commence when the lactated Ringer's solution was infused 120 minutes after the start of the experiment. It should also be noted that the drift in the total water fraction from approximately 77.5% to 75% before the infusion is not related to this infusion experiment, but is related to the base-line hemorrhage portion of the experiment. The results show that the method of the present embodiment correctly reflects the effect of the infusion by showing an increase in total tissue water fraction from approximately 75% to 79% while the infusion is continuing. These data suggest that the disclosed embodiment has a clear value as a monitor of rehydration therapy in a critical care setting.

In another embodiment of the present invention the water fraction, $f_w$, is estimated according to Equation (2) below, based on the measurement of reflectances, $R(\lambda)$ at three wavelengths and the empirically chosen calibration constants $c_0$, $c_1$ and $c_2$:

$$f_w = c_2 \log [R(\lambda_1)/R(\lambda_2)] + c_1 \log [R(\lambda_2)/R(\lambda_3)] + c_0 \quad (2)$$

Better absolute accuracy can be attained using Equation (2) which incorporates reflectance measurements at an additional wavelength. The results of in vitro experiments on excised skin indicate that the wavelength triple ($\lambda_1=1190$ nm, $\lambda_2=1170$ nm, $\lambda_3=1274$ mm) yields accurate estimates of total tissue water content based on Equation (2).

In yet another embodiment of the present invention the water fraction, $f_w$ is estimated according to Equation (3) below, based on the measurement of reflectances, $R(\lambda)$ at three wavelengths and the empirically chosen calibration constants $c_0$ and $c_1$:

$$f_w = c_1 \frac{\log[R(\lambda_1)/R(\lambda_2)]}{\log[R(\lambda_3)/R(\lambda_2)]} + c_0 \quad (3)$$

Figure 2:
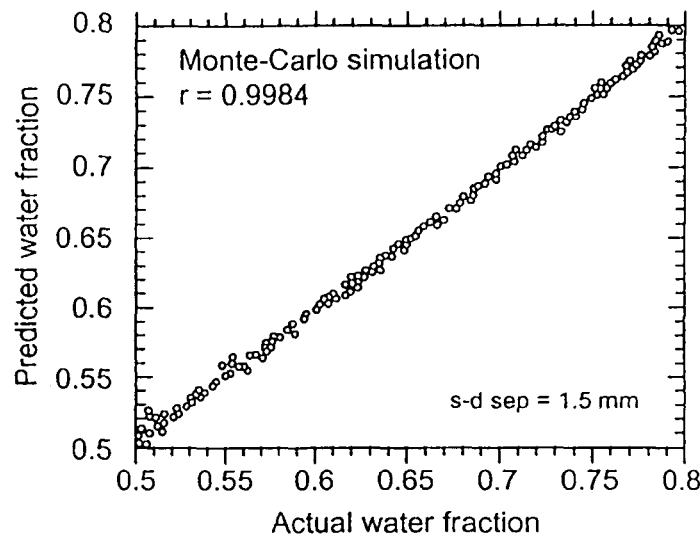
FIG. 2 is a graph showing an example regression for prediction of water from reflectances measured at three wavelengths.

Better absolute accuracy can be attained using Equations (3), as is attained using Equations (2), which also incorporates reflectance measurements at an additional wavelength. Numerical simulations as shown in FIG. 2 indicate that total tissue water accuracy better than +/−0.5% can be achieved using Equation (3), with reflectances measured at three closely spaced wavelengths: $\lambda_1=1710$ nm, $\lambda_2=1730$ nm, and $\lambda_3=1740$ nm. Additional numerical simulations indicate that accurate measurement of the lean tissue water content, $f_w^l$, can be accomplished using Equation (3), by combining reflectance measurements at 1125, 1185, and 1250 nm.

An additional embodiment of the present invention is directed towards the measurement of water content as a fraction of fat-free or lean tissue content, $f_w^l$.

Figure 7:
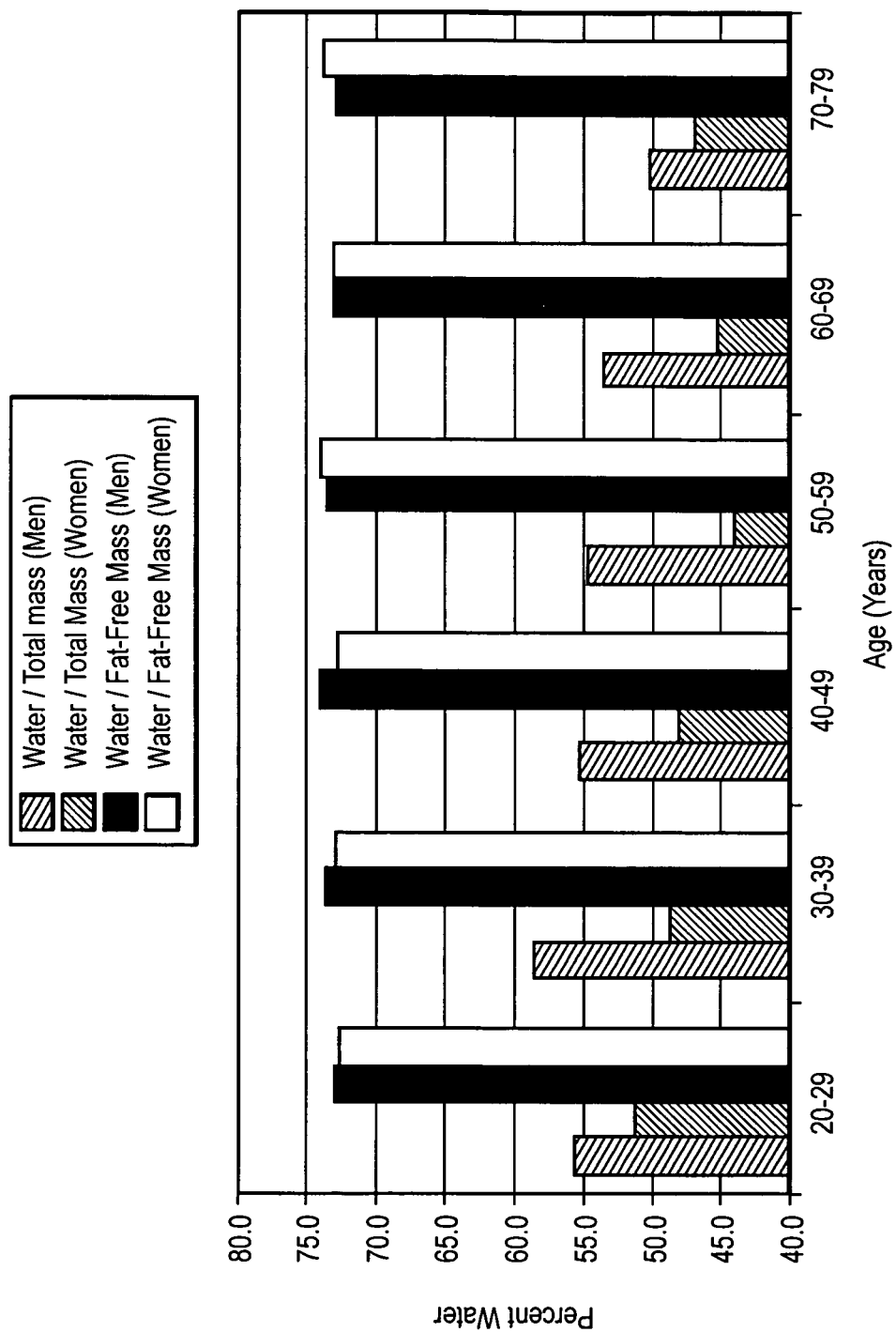
FIG. 7 is a bar graph of water content as a percentage of total and lean mass for men and women between the ages of 20 and 79.

Preferably, a tissue water monitor provides the clinician with an indication of whether the patient requires more, less, or no water to achieve a normo-hydrated state. Such a measurement may be less universally applicable than clinically desired when it is determined using an instrument that reports fractional water relative to either total body weight or total tissue content, due to the high variability of fat content across the human population. Fat contains very little water, so variations in the fractional fat content of the body lead directly to variations in the fractional water content of the body. When averaged across many patients, gender and age-related differences in fat content, result in systematic variations in water content, a fact that has been well-documented in the literature, as is shown for example in FIG. 7. Values shown in FIG. 7 are computed from Tables II-III of Cohn et al., J. Lab. Clin. Med. (1985) 105(3), 305-311.

Figure 8:
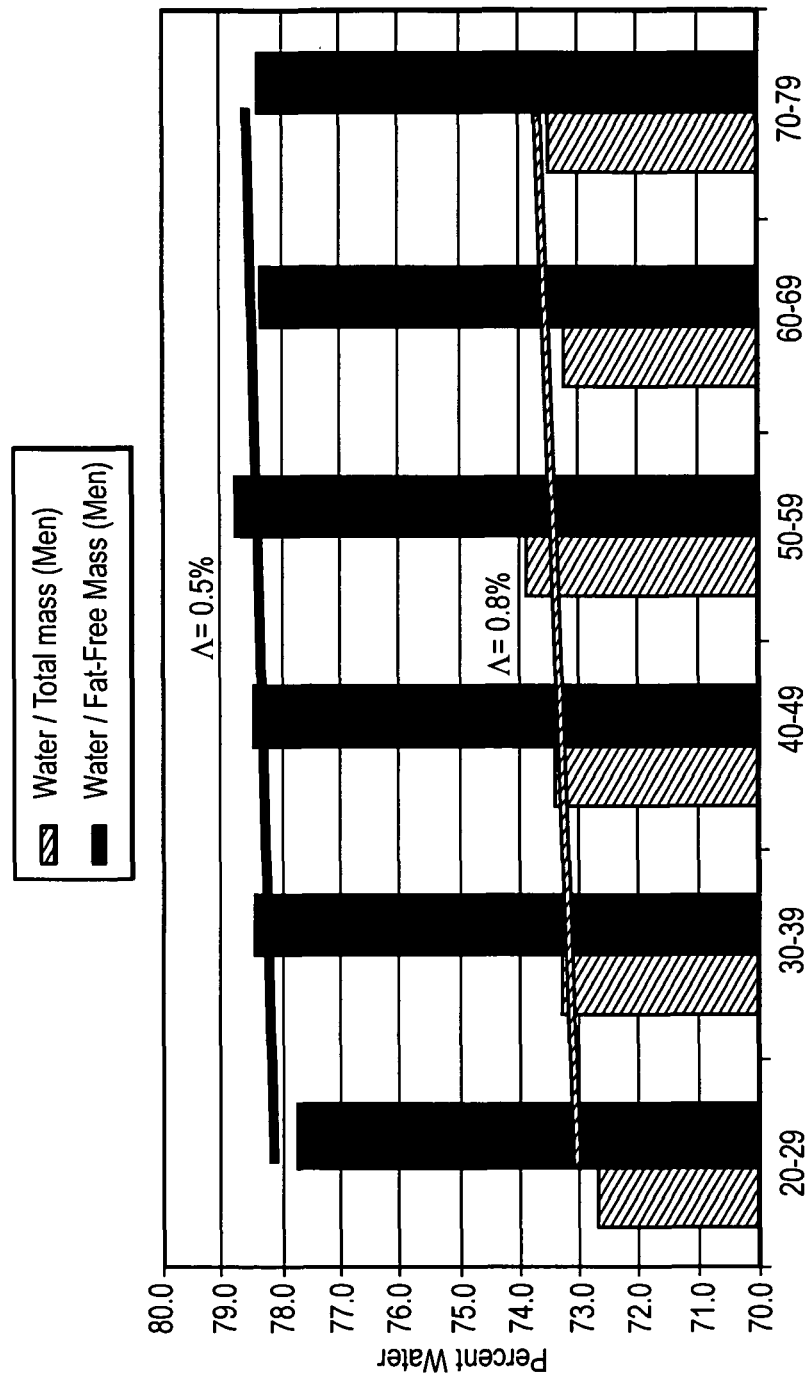
FIG. 8 is a bar graph of water content as a percentage of fat-free and fat-free-bone-free mass for men and women between the ages of 20 and 79.

In contrast, when fat is excluded from the calculation, the fractional water content, $f_w^l$, in healthy subjects, is consistent across both gender and age, as is shown, for example, in FIG. 7. This suggests that $f_w^l$, can be a more clinically useful measurement than $f_w$ for certain conditions. An additional reduction in the subject-to-subject variation in the "normal" level of fractional water content may observed if bone mass is excluded from the calculation, as may be seen in FIG. 8. This may be due to the fact that the bone content of the body tends to decrease with age (such as by osteoporosis). Due to the specified source-detector separations (e.g., 1-5 mm), wavelength ranges, and algorithms, the measurement of $f_w^l$ in tissue according to the embodiments of the present invention will be closely related to the whole body water content as a fraction of the fat-free-bone-free body content.

In yet another embodiment of the present invention, tissue water fraction, $f_w$, is estimated according to the following equation, based on the measurement of reflectances, $R(\lambda)$, at a plurality of wavelengths:

$$f_w = \frac{\left[\sum_{n=1}^{N} p_n \log\{R(\lambda_n)\}\right] - \left[\sum_{n=1}^{N} p_n\right] \log\{R(\lambda_{N+1})\}}{\left[\sum_{m=1}^{M} q_m \log\{R(\lambda_m)\}\right] - \left[\sum_{m=1}^{M} q_m\right] \log\{R(\lambda_{M+1})\}} \quad (4)$$

where $p_n$ and $q_m$ are calibration coefficients.

An obstacle to the quantification of tissue analytes is the high subject-to-subject variability of the scattering coefficient of tissue. Determination of the fractional tissue water in accordance with Equation (4) provides similar advantage as that of Equation (3) above, in that scattering variation is automatically cancelled, especially as long as the N+1 wavelengths are chosen from within the same wavelength band (950-1400 nm, 1500-1800 nm, or 2000-2300 nm). An explanation of the manner in which Equation (4) automatically cancels scattering variations is provided below.

Tissue reflectance can be modeled according to a modified form of the Beer-Lambert equation:

$$\log\{R(\lambda)\} = -l(\lambda) \sum_{j=1}^{J} c_j \varepsilon_j(\lambda) - \log\{I_0(\lambda)\} \quad (5)$$

where R is the tissue reflectance, l is the mean pathlength of light at wavelength $\lambda$, $\varepsilon_j$ and $c_j$ are the extinction coefficient and concentration of constituent j in the tissue, and $\log \{I_0(\lambda)\}$ is a scattering offset term. According to this model, the scattering dependence of tissue reflectance is due to the offset term, $\log \{I_0(\lambda)\}$, and the pathlength variation term, $l(\lambda)$. Since the scattering coefficient varies slowly with wavelength, by selecting all of the wavelengths from within the same wavelength band, the wavelength dependence of the scattering coefficient can be ignored to a good approximation. Under these conditions, by multiplying the log of the reflectance at wavelength N+1 (or M+1) by the negative of the sum of the coefficients used to multiply the log of the reflectances at the N (or M) other wavelengths, the scattering offset terms are cancelled in both the numerator and denominator of Equation (4). This can be seen, for example, by substituting Equation (5) into the numerator of Equation (4):

$$\left[\sum_{n=1}^{N} p_n \log\{R(\lambda_n)\}\right] - \left[\sum_{n=1}^{N} p_n\right] \log\{R(\lambda_{N+1})\} = \quad (6)$$

$$-l \sum_{n=1}^{N} \left[p_n \sum_{j=1}^{J} c_j \varepsilon_j(\lambda_n)\right] + l \left[\sum_{n=1}^{N} p_n\right] \sum_{j=1}^{J} c_j \varepsilon_j(\lambda_{N+1})$$

A review of Equation (6) shows that the scattering offset term has been cancelled, but the scattering dependent pathlength variation term, l, remains. When the numerator and denominator of Equation (4) are combined, the pathlength variation term is also cancelled, as shown in Equation (7):

$$f_w = \frac{-\sum_{n=1}^{N}\left[p_n \sum_{j=1}^{J} c_j \varepsilon_j(\lambda_n)\right] + \left[\sum_{n=1}^{N} p_n\right] \sum_{j=1}^{J} c_j \varepsilon_j(\lambda_{N+1})}{-\sum_{m=1}^{M}\left[q_m \sum_{j=1}^{J} c_j \varepsilon_j(\lambda_m)\right] + \left[\sum_{m=1}^{M} q_m\right] \sum_{j=1}^{J} c_j \varepsilon_j(\lambda_{M+1})} \qquad (7)$$

A review of Equation (7) shows that Equation (7) depends only on the concentrations and extinction coefficients of the constituents of tissue and on the calibration coefficients $p_n$ and $q_m$.

In addition to providing for variable scattering compensation, the methods using Equation (4) allow a more general implementation by relaxing some of the constraints that are imposed by the use of Equation (3), above. For example:

(a) In order to provide a certain level of accuracy for measurement of $f_w$, the numerator in Equation (3) may need to be sensitive to changes in water concentration but insensitive to changes in all other tissue constituents. For example, Equation (3) may require that the absorbance of all tissue constituents besides water (e.g. lipid, non-heme protein, hemoglobin) are nearly equal at wavelengths 1 and 2. This constraint is removed in Equation (4), where the coefficients $p_n$ are chosen to cancel out absorbance by all tissue constituents other than water.

(b) In order to provide a certain level accuracy for measurement of $f_w$, the denominator in Equation (3) may need to be equally sensitive to concentration changes of all tissue constituents to which the water fraction is to be normalized. In addition, Equation (3) may require that the absorbance be equal at wavelengths 2 and 3 for all tissue constituents to be excluded from the water fraction normalization. This constraint is removed in Equation (4), where the coefficients, $q_m$, can be chosen to cancel the absorbance contribution due to certain constituents, while equalizing the absorbance sensitivity to the remaining tissue constituents.

In the case of measurement of the water fraction in lean tissue, $f_w^l$, the coefficients, $p_n$, in the numerator of Equation (4) are chosen to cancel the contribution from all of the major light-absorbing constituents of tissue, except water. Similarly, the coefficients, $q_m$, in the denominator of Equation (4) are chosen to cancel the contribution from all tissue constituents other than water and protein. In addition, the coefficients, $q_m$, are chosen to equalize the sensitivity of the denominator to changes in water and protein on a volume fractional basis. By computing the ratio of these two terms, the result is a fractional volume measurement of water concentration in lean tissue.

In addition, application of Equation (4) to the measurement of fractional water content in total tissue volume, $f_w^T$, is accomplished by choosing the coefficients in the denominator of Equation (4), $q_m$, so that all tissue constituents (including lipid) are equalized on a fractional volume basis.

Figure 9:
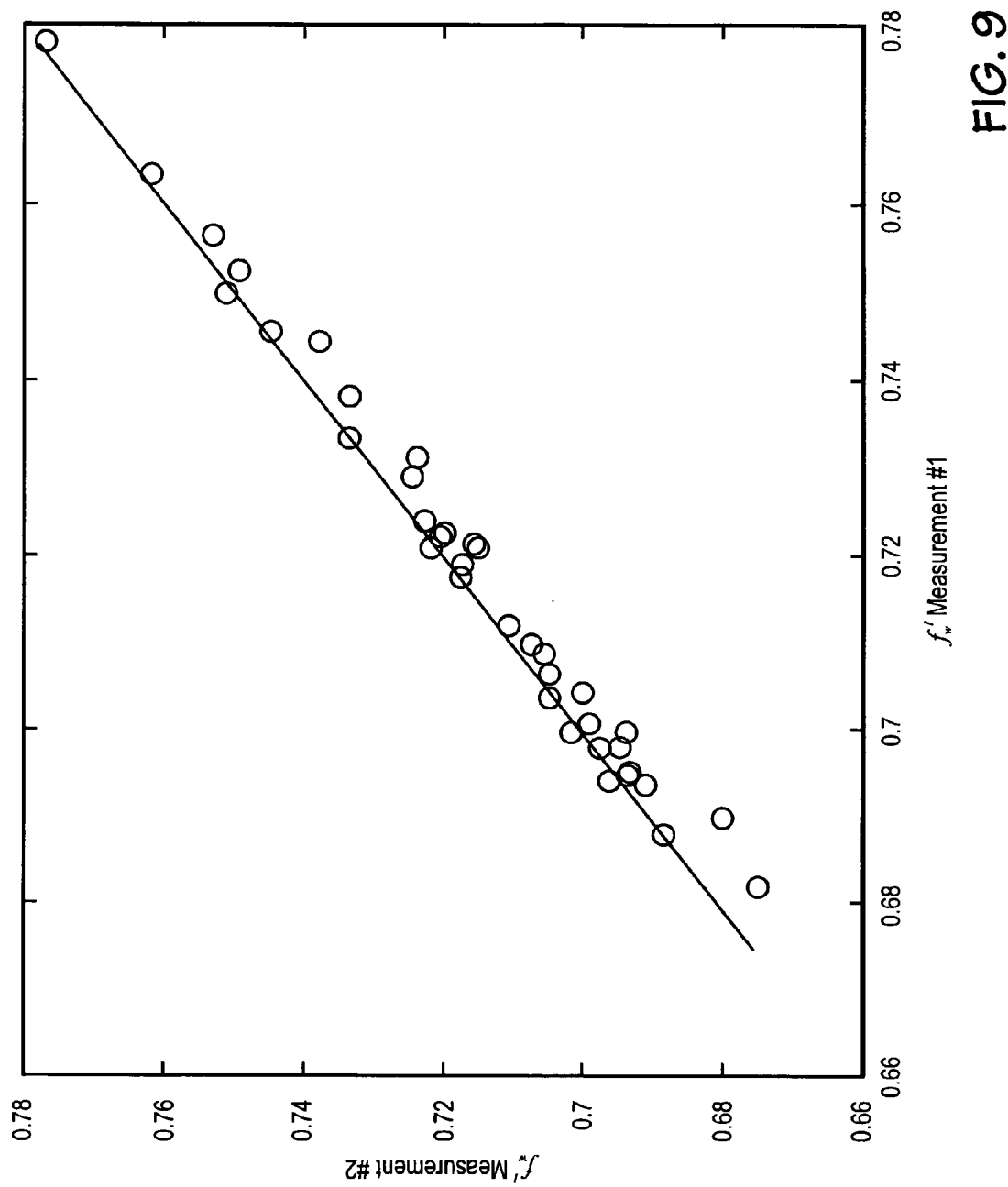
FIG. 9 is a graph of the correlation between separate fat-free or lean volume water fraction ("$f_w^l$") measurements on the same patient.

By relaxing some of the constraints imposed by Equation (3), the use of Equation (4) can be expected to produce a more accurate prediction of fractional tissue water content, for the reasons set forth above. Various wavelength combinations may be used based on the criteria disclosed above. In order to select one wavelength combination for use with Equation (4) for the purpose of measuring fractional water content in lean tissue, $f_w^l$, extinction coefficients of the major absorbing constituents of tissue (water, non-heme protein, lipid, and hemoglobin) were experimentally measured and various wavelength combinations of these were applied to a numerical model of tissue absorbance. The reproducibility of the algorithms incorporating the most promising of these wavelength combinations were then compared using real tissue data. The real tissue data were collected from 37 different volunteers at a local hospital, with Institutional Review Board (IRB) approval. The sensor measured reflected light from the pad of the finger, with a source-detector spacing of approximately 2.5 mm. The sensor was completely removed from the tissue between each pair of measurements. One such preferred algorithm combines measurements at 4 wavelengths, namely: 1180, 1245, 1275, and 1330 nm. Using this selection of wavelengths, the measurement-to-measurement reproducibility, as shown in FIG. 9, is 0.37%, indicating high reproducibility of the tissue water measurements using the methods disclosed herein.

In addition to providing a method for measuring tissue water fraction, the method in accordance with Equation (4) above, also has general utility for the fractional quantification of analytes in tissue. In general, by appropriate choice of wavelengths and coefficients, Equation (4) is extendible to the fractional concentration measurement of any tissue constituent or combination of constituents in tissue with respect to any other constituent or combination of constituents. For example, this equation is also applicable for the determination of the fractional hemoglobin content in tissue.

Thus, in one embodiment of the present invention, the fractional volume of total hemoglobin in tissue is determined using Equation (4) by combining reflectance measurements at wavelengths where hemoglobin is strongly absorbing with reflectance measurements where the remaining tissue constituents (such as water, lipid, and non-protein) are strongly absorbing. The coefficients, $p_n$, in the numerator of Equation (4) are chosen to cancel the absorbance contributions from all tissue constituents except total hemoglobin. The coeffients, $q_m$, in the denominator of Equation (4) are chose to equalize the absorbance contributions of all major tissue constituents, on a volume fractional basis. One specific wavelength combination for accomplishing this measurement is 805 nm, 1185 nm, and 1310 nm. At 805 nm the absorbance by the oxy- and deoxyhemoglobin are approximately equal. At 1185 nm, the absorbance of water, non-heme protein, and lipid, are nearly equal on a fractional volume basis. At 1300 nm the tissue absorbance will be dominated by water.

In another embodiment of the present invention, measurement of fractional concentrations of different species of hemoglobin in tissue is performed. In general, the method provides a means of measuring the fractional concentration of hemoglobin in a first set comprised of one or more species of hemoglobin with respect to the concentration of hemoglobin in a second set comprised of one or more hemoglobin species in tissue. The coefficients, $p_n$, in the numerator of Equation (4) are chosen to cancel the absorbance contributions from all tissue constituents except the hemoglobin species included in set 1. The coeffients, $q_m$, in the denominator of Equation (4) are chose to equalize the absorbance contributions from all tissue constituents except the hemoglobin species included in set 2. Sets 1 and 2 are subsets of hemoglobin species that are present in the body tissue or blood. For example, such hemoglobin species include oxyhemoglobin, deoxyhemoglobin, carboxyhemoglobin, methemoglobin, sulfhemoglobin and, so on. And in general, as used herein, other physiological parameters have other subsets of constituents each being capable of absorbing at different wavelengths. In the case where set 1 is comprised of oxyhemoglobin and set 2 is comprised of oxy- and deoxyhemoglobin, a specific wavelength combination for accomplishing the measurement is 735, 760, and 805 nm.

Individuals skilled in the art of near-infrared spectroscopy would recognize that, provided that the aforementioned guidelines are followed, additional terms can be added to Equations (1)-(4) and which may be used to incorporate reflectance measurements made at additional wavelengths and thus improve accuracy further.

Figure 3:
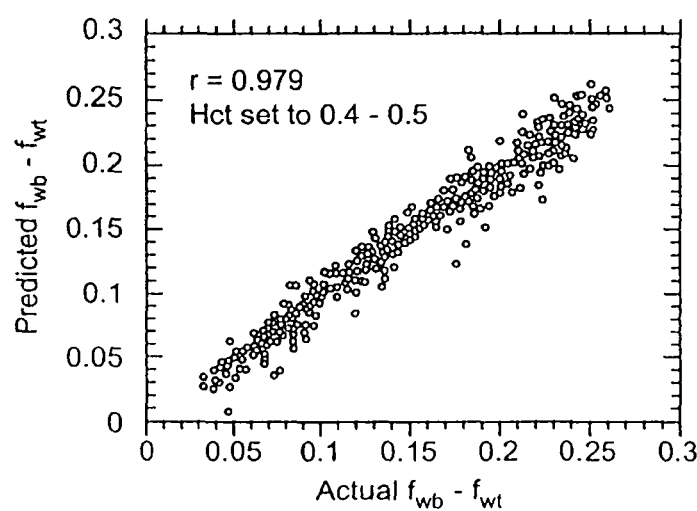
FIG. 3 is a graph showing an example regression of a two-wavelength algorithm for determination of the difference between the intravascular and extravascular water fraction from pulsatile reflectances measured at two wavelengths.

An additional embodiment of the disclosed invention provides the ability to quantify shifts of fluid into and out of the bloodstream through a novel application of pulse spectrophotometry. This additional embodiment takes advantage of the observation that pulsations caused by expansion of blood vessels in the skin as the heart beats produce changes in the reflectance at a particular wavelength that are proportional to the difference between the effective absorption of light in the blood and the surrounding interstitial tissues. Numerical simulation indicate that, if wavelengths are chosen at which water absorption is sufficiently strong, the difference between the fractions of water in the blood, $f_w^{IV}$ and surrounding tissue, $f_w^{EV}$ is proportional to the ratio of the dc-normalized reflectance changes ($\Delta R/R$) measured at two wavelengths, according to Equation (8) below:

$$f_w^{EV} - f_w^{IV} = c_1 \frac{(\Delta R/R)_{\lambda_1}}{(\Delta R/R)_{\lambda_2}} + c_0, \qquad (8)$$

where $c_0$ and $c_1$ are empirically determined calibration constants. This difference, integrated over time, provides a measure of the quantity of fluid that shifts into and out of the capillaries. FIG. 3 shows the prediction accuracy expected for the wavelength pair $\lambda_1=1320$ nm and $\lambda_2=1160$ nm.

An additional embodiment of the present invention is directed towards the measurement of water balance index, Q, such that:

$$Q = \frac{f_w^{IV} - f_w^{EV}}{f_h^{IV}} = a_1 \frac{(\Delta R/R)_{\lambda_1}}{(\Delta R/R)_{\lambda_2}} + a_0 \qquad (9)$$

where $f_h^{IV}$ is the fractional volume concentration of hemoglobin in the blood, and $a_o$ and $a_1$ are calibration coefficients. The use of Equation (9) to determine a water balance is equivalent to using Equation (8) above, where $f_h^{IV}$ is set equal to 1. However, using Equation (9) provides for a more accurate determination by not neglecting the influence of $f_h^{IV}$ on the derived result. The effect of this omission can be understood by allowing total hemoglobin to vary over the normal physiological range and computing the difference between the results provided by Equation (9) when $f_h^{IV}$ is fixed or allowed to vary. For example, when calculations were performed with $f_w^{EV}$ fixed at 0.65, $f_w^{IV}$ varying between 0.75 and 0.80, and $f_h^{IV}$ varying between 0.09 and 0.135 or held fixed at 0.112, the resulting error was as large as +/−20%. In situations of extreme blood loss or vascular fluid overload (hypo- or hypervolemia) the error could be larger.

The quantity Q, provided by Equation (9) may be combined with a separate measurement of fractional hemoglobin concentration in blood, $f_h^{IV}$, (such as may be provided by standard clinical measurements of hematocrit or total hemoglobin) in order to provide a measure of the difference between the intravascular and extravascular water content, $f_w^{IV}-f_w^{EV}$. Alternatively, the quantity Q, may have clinical utility without further manipulation. For example, by providing a simultaneous measurement of both Q and fractional tissue water (either $f_w$ or $f_w^l$), the embodiments of the present invention enable the provision of a clinical indication of changes in both volume and osmolarity of body fluids. Table 1 lists the 6 combinations of volume and osmolarity changes in body fluids that are clinically observed (from Physiology, $2^{nd}$ Edition, Linda S. Costanzo, Williams and Wilkins, Baltimore, 1998, pg. 156), and the expected direction and magnitude of the resultant change in fractional volume of water in blood ($f_w^{IV}$), the fractional volume of water in tissue ($f_w^{EV}$), the fractional volume of hemoglobin in blood ($f_h^{IV}$), the numerator of Q ($Q_n$), the inverse of the denominator of Q ($1/Q_d$), the combined result ($Q_n/Q_d=Q$), and the fractional volume of water in lean tissue, $f_w^l$. Taking the first row of Table 1 as an example, the result of isosmotic volume expansion, such as may be brought about by infusion with isotonic saline, would result in an increase in the fraction of water in blood ($f_w^{IV}$), a small increase in the extravascular water fraction ($f_w^{EV}$), and a large decrease in the fractional concentration of hemoglobin in the blood ($f_h^{IV}$). The combined effect of these 3 factors would result in a large increase in Q. A small increase in the fraction of water in the lean tissue, $f_w^l$, would also be expected. Notice that when Q and $f_w^l$ are viewed in combination, they provide unique signatures for each of the 6 types of fluid balance change listed in Table 1. An instrument providing these measurements in a non-invasive and continuous fashion is thus able to provide a powerful tool for the monitoring of tissue water balance.

TABLE 1

Expected changes in Q and $f_w^l$ resulting from changes in body fluid volume and osmolarity

| Type | Example | $f_w^{IV}$ | $f_w^{EV}$ | $f_h^{IV}$ | $Q_n$ | $1/Q_d$ | Q | $f_w^l$ |
|---|---|---|---|---|---|---|---|---|
| Isosmotic volume expansion | Isotonic NaCl Infusion | ↑ | ↑ | ↓ | ↑ | ↑ | ↑ | ↑ |
| Isosmotic volume contraction | Diarrhea | ↓ | ↓ | ↑ | ↓ | ↓ | ↓ | ↑ |
| Hyperosmotic volume expansion | High NaCl intake | ↑ | ↓ | ↓ | ↑ | ↑ | ↑ | 0 |
| Hyperosmotic volume contraction | Sweating, Fever | ↓ | ↓ | ↑ | 0 | ↓ | ↓ | ↓ |
| Hyposmotic volume contraction | SIADH | ↑ | ↑ | ↓ | 0 | ↑ | ↑ | ↑ |
| Hyposmotic volume contraction | Adrenal Insufficiency | ↓ | ↑ | ↑ | ↓ | ↓ | ↓ | 0 |

Figure 4:
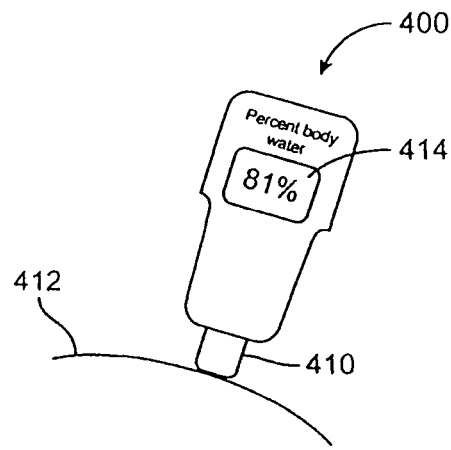
FIG. 4 is a diagram of an intermittent-mode version of a fluid monitor.
Figure 5:
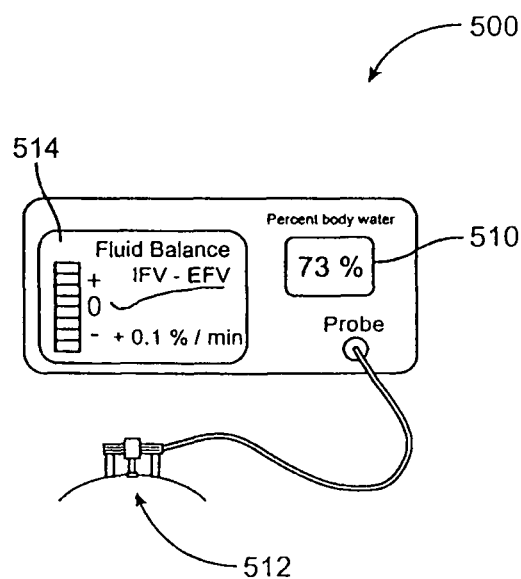
FIG. 5 is a diagram of a continuous-mode version of a fluid monitor.

FIGS. 4 and 5 show diagrams of two different versions of an instrument for measuring the amount of water in body tissues. The simplest version of the instrument 400 shown in FIG. 4 is designed for handheld operation and functions as a spot checker. Pressing the spring-loaded probe head 410 against the skin 412 automatically activates the display of percent tissue water 414. The use of the spring-loaded probe head provides the advantages of automatically activating the display device when needed and turning the device off when not in use, thereby extending device and battery life. Moreover, this unique use of a spring-loaded probe also provides the variable force needed to improve the reliability of measurements. Percent tissue water represents the absolute percentage of water in the skin beneath the probe (typically in the range 0.6-0.9). In one embodiment of the present invention, the force exerted by a spring or hydraulic mechanism (not shown) inside the probe head 410 is minimized, so that the fluid content of the tissue beneath the probe is not perturbed by its presence. In this manner, the tissue water fraction, including both intravascular and extravascular fluid fractions is measured. In another embodiment of the invention, the force exerted by the probe head is sufficient to push out most of the blood in the skin below the probe to allow measurement of only the extravascular fluid fraction. A pressure transducer (not shown) within the probe head 410 measures the compressibility of the skin for deriving an index of the fraction of free (mobile) water.

The more advanced version of the fluid monitor 500 shown in FIG. 5 is designed for use as a critical-care monitor. In addition to providing a continuous display of the volume fraction of water 510 at the site of measurement 512, it also provides a trend display of the time-averaged difference between the intravascular fluid volume ("IFV") and extravascular fluid volume ("EFV") fractions (e.g., IFV-EFV=$f_w^{IV}$-$f_w^{EV}$) 514 or the quantity Q (as defined above with reference to Equation (9), updated every few seconds. This latter feature would give the physician immediate feedback on the net movement of water into or out of the blood and permit rapid evaluation of the effectiveness of diuretic or rehydration therapy. To measure the IFV-EFV difference or Q, the monitor records blood pulses in a manner similar to a pulse oximeter. Therefore, placement of the probe on the finger or other well-perfused area of the body would be required. In cases in which perfusion is too poor to obtain reliable pulse signals, the IFV-EFV or Q display would be blanked, but the tissue water fraction ($f_w$) would continue to be displayed. A mechanism for mechanically inducing the pulse is built into the probe to improve the reliability of the measurement of IFV-EFV or Q under weak-pulse conditions.

Figure 6:
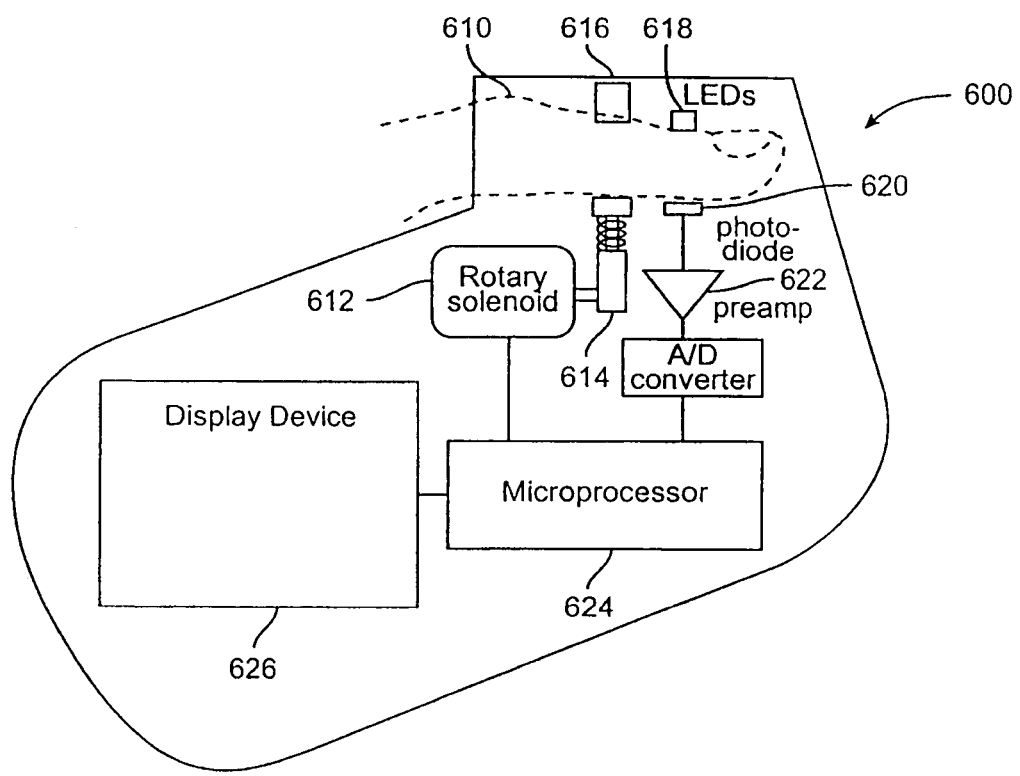
FIG. 6 is a block diagram of a handheld apparatus for noninvasive measurement and display of tissue water.

FIG. 6. is a block diagram of a handheld device 600 for measuring tissue water fraction, as well as shifts in water between the IFV and EFV compartments, or a measurement of Q, with a pulse inducing mechanism. Using this device 600, patient places his/her finger 610 in the probe housing. Rotary solenoid 612 acting through linkage 614 and collar 616 induces a mechanical pulse to improve the reliability of the measurement of IFV-EFV or Q. LEDs 618 emit light at selected wavelengths and photodiode 620 measure the transmitted light. Alternately, the photodiode 620 can be placed adjacent to the LEDs to allow for the measurement of the reflectance of the emitted light. Preamplifier 622 magnifies the detected signal for processing by the microprocessor 624. Microprocessor 624, using algorithms described above, determines the tissue water fraction ($f_w$) (such as in the total tissue volume ($f_w^T$), within the lean tissue volume ($f_w^l$), and/or within the IFV ($f_w^{IV}$) and the EFV ($f_w^{EV}$)), as well as shifts in water between the IFV and EFV (such as IFV-EFV or Q), and prepares this information for display on display device 626. Microprocessor 624 is also programmed to handle the appropriate timing between the rotary solenoid's operation and the signal acquisition and processing. In one embodiment, a means is provided for the user to input the fractional hemoglobin concentration ($f_h^{IV}$) or a quantity proportional to $f_h^{IV}$ (such as hematocrit or total hemoglobin) in order to convert Q into IFV-EFV. The design of the device and the microprocessor integrates the method and apparatus for reducing the effect of noise on measuring physiological parameters as described in U.S. Pat. No. 5,853,364, assigned to Nellcor Puritan Bennett, Inc., the entire disclosure of which is hereby incorporated herein by reference. Additionally, the design of the device and the microprocessor also integrates the electronic processor as described in U.S. Pat. No. 5,348,004, assigned to Nellcor Incorporated, the entire disclosure of which is hereby incorporated herein by reference.

As will be understood by those skilled in the art, other equivalent or alternative methods for the measurement of the water fraction within tissue ($f_w$), as well as shifts in water between the intravascular and extravascular compartments, IVF-EVF or Q, according to the embodiments of the present invention can be envisioned without departing from the essential characteristics thereof. For example, the device can be operated in either a handheld or a tabletop mode, and it can be operated intermittently or continuously. Moreover, individuals skilled in the art of near-infrared spectroscopy would recognize that additional terms can be added to the algorithms used herein to incorporate reflectance measurements made at additional wavelengths and thus improve accuracy further. Also, light sources or light emission optics other then LED's including and not limited to incandescent light and narrowband light sources appropriately tuned to the desired wavelengths and associated light detection optics may be placed within the probe housing which is placed near the tissue location or may be positioned within a remote unit; and which deliver light to and receive light from the probe location via optical fibers. Additionally, although the specification describes embodiments functioning in a back-scattering or a reflection mode to make optical measurements of reflectances, other embodiments can be working in a forward-scattering or a transmission mode to make these measurements. These equivalents and alternatives along with obvious changes and modifications are intended to be included within the scope of the present invention. Accordingly, the foregoing disclosure is intended to be illustrative, but not limiting, of the scope of the invention which is set forth in the following claims.

What is claimed is:

1. A device for determining an estimate of body water content, comprising:

a processing device configured to process a signal indicative of radiation detected from lean tissue of a patient to compute the estimate of body tissue water content, wherein the estimate is correlative to a computed fractional water content of the lean tissue, wherein the computed fractional water content of the lean tissue ($f_w^l$) is determined such that $$f_w^l = \frac{\left[\sum_{n=1}^{N} p_n \log\{R(\lambda_n)\}\right] - \left[\sum_{n=1}^{N} p_n\right] \log\{R(\lambda_{N+1})\}}{\left[\sum_{m=1}^{M} q_m \log\{R(\lambda_m)\}\right] - \left[\sum_{m=1}^{M} q_m\right] \log\{R(\lambda_{M+1})\}},$$

and where:

$p_n$ and $q_m$ are calibration coefficients;

$R(\lambda)$ is a measure of the detected radiation at a given wavelength; and n=1–N and m=1–M represent indices for a plurality of wavelengths of the detected radiation which may comprise of the same or different combinations of wavelengths.

2. The device of claim 1, wherein the computation of fractional water content of the lean tissue substantially excludes fat content and bone content of the patient.

3. The device of claim 1, comprising a display device coupled to the processing device to display the estimate of body tissue water content.

4. The device of claim 1, wherein the estimate of body tissue water content comprises a ratio of the body tissue of the patient and the lean tissue of the patient.

5. The device of claim 1, wherein the processing device receives and compares at least a first set and a second set of optical measurements, where the first set of optical measurements corresponds to the detected radiation having an absorption primarily due to water and non-heme proteins, and where the second set of optical measurements corresponds to the detected radiation having an absorption primarily due to water, and where a comparison of the first set and the second set of optical measurements provides a measure of a lean water fraction of the lean tissue.

6. The device of claim 1, wherein the processing device receives and compares at least two sets of optical measurements, where the at least two sets of optical measurements are based on detected radiation from at least two wavelengths and which are combined to form a ratio of combinations of the detected radiation.

7. The device of claim 6, wherein the processing device forms a weighted summation of the combinations.

8. The device of claim 1, wherein the processing device receives and compares at least two sets of optical measurements from at least two different wavelengths, where absorption of light at the at least two different wavelengths is primarily due to water which is in vascular blood of the patient and in extravascular tissue of the patient, and where a ratio of the at least two measurements provides a measure proportional to a difference between fractions of water in the blood and a surrounding tissue location.

9. The device of claim 1, wherein M and N are both equal to 3, wherein wavelengths indexed by m and n comprise of the same combination of wavelengths, and wherein first, second, third and fourth wavelengths are approximately 1180, 1245, 1275 and 1330 nm respectively.

10. A method for determining a body tissue water content metric as a fraction of lean tissue content of a patient, comprising:

processing radiation received from a tissue location of the patient to compute the body tissue water content metric, wherein the body tissue water content metric ($f_w^l$) is determined such that $$f_w^l = \frac{\left[\sum_{n=1}^{N} p_n \log\{R(\lambda_n)\}\right] - \left[\sum_{n=1}^{N} p_n\right] \log\{R(\lambda_{N+1})\}}{\left[\sum_{m=1}^{M} q_m \log\{R(\lambda_m)\}\right] - \left[\sum_{m=1}^{M} q_m\right] \log\{R(\lambda_{M+1})\}},$$

and where:

$p_n$ and $q_m$ are calibration coefficients;

$R(\lambda)$ is a measure of the received radiation at a wavelength;

n=1–N and m=1–M represent indexes for a plurality of wavelengths which may comprise of the same or different combinations of wavelengths.

11. A method of determining a physiological parameter in a human tissue location, comprising:

processing radiation received from the human tissue location to compute the physiological parameter, wherein the physiological parameter is determined such that it is equal to $$\frac{\left[\sum_{n=1}^{N} p_n \log\{R(\lambda_n)\}\right] - \left[\sum_{n=1}^{N} p_n\right] \log\{R(\lambda_{N+1})\}}{\left[\sum_{m=1}^{M} q_m \log\{R(\lambda_m)\}\right] - \left[\sum_{m=1}^{M} q_m\right] \log\{R(\lambda_{M+1})\}},$$

and where:

$p_n$ and $q_m$ are calibration coefficients;

$R(\lambda)$ is a measure of the received radiation at a wavelength;

n=1–N and m=1–M represent indexes for a plurality of wavelengths which may comprise of the same or different combinations of wavelengths.

12. The method of claim 11, wherein the physiological parameter comprises a tissue water fraction of the tissue location.

13. The method of claim 11, wherein the physiological parameter comprises an oxygen saturation value of the tissue location.

14. The method of claim 11, wherein the physiological parameter comprises a fractional hemoglobin concentration of the tissue location.

15. The method of claim 11, wherein the physiological parameter comprises a fractional concentration of hemoglobin in a first set comprised of one or more species of hemoglobin with respect to a concentration of hemoglobin in a second set comprised of one or more hemoglobin species in the tissue location.

16. The method of claim 15 wherein the coefficients, $p_n$, are chosen to substantially cancel absorbance contributions from all tissue constituents except the hemoglobin species included in the first set, and wherein the coeffients, $q_m$, are chosen to substantially cancel absorbance contributions from all tissue constituents except the hemoglobin species included in the second set.

* * * * *